US012564365B2

(12) United States Patent
Gkanatsios et al.

(10) Patent No.: US 12,564,365 B2
(45) **Date of Patent: *Mar. 3, 2026**

(54) SYSTEM AND METHOD FOR GENERATING AND DISPLAYING TOMOSYNTHESIS IMAGE SLABS

(71) Applicant: Hologic, Inc., Marlborough, MA (US)

(72) Inventors: Nikolaos Gkanatsios, Newtown, CT (US); Haili Chui, Fremont, CA (US); Xiangwei Zhang, Fremont, CA (US)

(73) Assignee: Hologic, Inc., Marlborough, MA (US)

( * ) Notice: Subject to any disclaimer, the term of this patent is extended or adjusted under 35 U.S.C. 154(b) by 72 days.

This patent is subject to a terminal disclaimer.

(21) Appl. No.: 18/469,775

(22) Filed: Sep. 19, 2023

(65) Prior Publication Data

US 2024/0138792 A1 May 2, 2024

Related U.S. Application Data

(63) Continuation of application No. 17/869,408, filed on Jul. 20, 2022, now Pat. No. 11,801,025, which is a
(Continued)

(51) Int. Cl.
*G06K 9/00* (2022.01)
*A61B 6/00* (2006.01)
(Continued)

(52) U.S. Cl.
CPC .............. *A61B 6/502* (2013.01); *A61B 6/025* (2013.01); *A61B 6/5223* (2013.01);
(Continued)

(58) Field of Classification Search
CPC .......... A61B 6/469; G06T 2207/10112; G06T 15/08
See application file for complete search history.

(56) References Cited

U.S. PATENT DOCUMENTS 3,502,878 A 3/1970 Stewart
3,863,073 A 1/1975 Wagner
(Continued)

FOREIGN PATENT DOCUMENTS

AU 2014339982 4/2015
CN 1802121 A 7/2006
(Continued)

OTHER PUBLICATIONS

Perek, S. et al., "Siamese network for dual-view mammography mass matching", Image Analysis for Moving Organ, Breast & Thoracic Images: 3rd Int'l Workshop, RAMBO 2018, 4th Int'l Workshop, BIA 2018, and 1st Int'l Workshop, TIA 2018, Proceedings 3.Springer International Publishing, 2018.
(Continued)

*Primary Examiner* — Hadi Akhavannik
(74) *Attorney, Agent, or Firm* — Merchant & Gould P.C.

(57) ABSTRACT

A system for processing breast tissue images includes an image processing computer and a user interface operatively coupled to the image processing computer, wherein the image processing computer is configured to obtain image data of breast tissue, processing the image data to generate a set of reconstructed image slices, the reconstructed image slices collectively depicting the breast tissue, process respective subsets of the reconstructed image slices to generate a set of image slabs, each image slab comprising a synthesized 2D image of a portion of the breast tissue obtained from a respective subset of the set of reconstructed image slices.

20 Claims, 9 Drawing Sheets

Related U.S. Application Data continuation of application No. 16/792,127, filed on Feb. 14, 2020, now Pat. No. 11,419,565, which is a continuation of application No. 16/143,181, filed on Sep. 26, 2018, now Pat. No. 10,575,807, which is a continuation of application No. 15/120,911, filed as application No. PCT/US2015/017713 on Feb. 26, 2015, now Pat. No. 10,111,631.

(60) Provisional application No. 61/946,417, filed on Feb. 28, 2014.

(51) Int. Cl.
| | |
|---|---|
| *A61B 6/02* | (2006.01) |
| *A61B 6/50* | (2024.01) |
| *G06T 11/00* | (2006.01) |
| *G06T 11/60* | (2006.01) |

(52) U.S. Cl.
CPC ............ *G06T 11/008* (2013.01); *G06T 11/60* (2013.01); *G06T 2207/10081* (2013.01); *G06T 2207/20021* (2013.01); *G06T 2207/20076* (2013.01); *G06T 2207/30068* (2013.01); *G06T 2210/41* (2013.01)

(56) References Cited

U.S. PATENT DOCUMENTS

| | | |
|---|---|---|
| 3,971,950 A | 7/1976 | Evans et al. |
| 4,160,906 A | 7/1979 | Daniels |
| 4,310,766 A | 1/1982 | Finkenzeller et al. |
| 4,496,557 A | 1/1985 | Malen et al. |
| 4,559,557 A | 12/1985 | Keyes |
| 4,559,641 A | 12/1985 | Caugant et al. |
| 4,706,269 A | 11/1987 | Reina et al. |
| 4,727,565 A | 2/1988 | Ericson |
| 4,744,099 A | 5/1988 | Huettenrauch |
| 4,773,086 A | 9/1988 | Fujita |
| 4,773,087 A | 9/1988 | Plewes |
| 4,819,258 A | 4/1989 | Kleinman et al. |
| 4,821,727 A | 4/1989 | Levene et al. |
| 4,907,156 A | 3/1990 | Doi et al. |
| 4,969,174 A | 11/1990 | Schied |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,099,846 A | 3/1992 | Hardy |
| 5,129,911 A | 7/1992 | Siczek et al. |
| 5,133,020 A | 7/1992 | Giger et al. |
| 5,163,075 A | 11/1992 | Lubinsky |
| 5,164,976 A | 11/1992 | Scheid et al. |
| 5,199,056 A | 3/1993 | Darrah |
| 5,219,351 A | 6/1993 | Teubner |
| 5,240,011 A | 8/1993 | Assa |
| 5,279,309 A | 1/1994 | Taylor et al. |
| 5,280,427 A | 1/1994 | Magnusson |
| 5,289,520 A | 2/1994 | Pellegrino et al. |
| 5,343,390 A | 8/1994 | Doi et al. |
| 5,359,637 A | 10/1994 | Webbe |
| 5,365,562 A | 11/1994 | Toker |
| 5,386,447 A | 1/1995 | Siczek |
| 5,415,169 A | 5/1995 | Siczek et al. |
| 5,426,685 A | 6/1995 | Pellegrino et al. |
| 5,452,367 A | 9/1995 | Bick |
| 5,491,627 A | 2/1996 | Zhang et al. |
| 5,499,097 A | 3/1996 | Ortyn et al. |
| 5,506,877 A | 4/1996 | Niklason et al. |
| 5,526,394 A | 6/1996 | Siczek |
| 5,539,797 A | 7/1996 | Heidsieck et al. |
| 5,553,111 A | 9/1996 | Moore |
| 5,592,562 A | 1/1997 | Rooks |
| 5,594,769 A | 1/1997 | Pellegrino et al. |
| 5,596,200 A | 1/1997 | Sharma |
| 5,598,454 A | 1/1997 | Franetzki |
| 5,609,152 A | 3/1997 | Pellegrino et al. |
| 5,627,869 A | 5/1997 | Andrew et al. |
| 5,642,433 A | 6/1997 | Lee et al. |
| 5,642,441 A | 6/1997 | Riley et al. |
| 5,647,025 A | 7/1997 | Frost et al. |
| 5,657,362 A | 8/1997 | Giger et al. |
| 5,660,185 A | 8/1997 | Shmulewitz et al. |
| 5,668,889 A | 9/1997 | Hara |
| 5,671,288 A | 9/1997 | Wilhelm et al. |
| 5,709,206 A | 1/1998 | Teboul |
| 5,712,890 A | 1/1998 | Spivey |
| 5,719,952 A | 2/1998 | Rooks |
| 5,735,264 A | 4/1998 | Siczek et al. |
| 5,757,880 A | 5/1998 | Colomb |
| 5,763,871 A | 6/1998 | Ortyn et al. |
| 5,769,086 A | 6/1998 | Ritchart et al. |
| 5,773,832 A | 6/1998 | Sayed et al. |
| 5,803,912 A | 9/1998 | Siczek et al. |
| 5,818,898 A | 10/1998 | Tsukamoto et al. |
| 5,828,722 A | 10/1998 | Ploetz |
| 5,835,079 A | 11/1998 | Shieh |
| 5,841,124 A | 11/1998 | Ortyn et al. |
| 5,872,828 A | 2/1999 | Niklason et al. |
| 5,875,258 A | 2/1999 | Ortyn et al. |
| 5,878,104 A | 3/1999 | Ploetz |
| 5,878,746 A | 3/1999 | Lemelson et al. |
| 5,896,437 A | 4/1999 | Ploetz |
| 5,941,832 A | 8/1999 | Tumey |
| 5,954,650 A | 9/1999 | Saito |
| 5,986,662 A | 11/1999 | Argiro |
| 6,005,907 A | 12/1999 | Ploetz |
| 6,022,325 A | 2/2000 | Siczek et al. |
| 6,067,079 A | 5/2000 | Shieh |
| 6,075,879 A | 6/2000 | Roehrig et al. |
| 6,091,841 A | 7/2000 | Rogers |
| 6,091,981 A | 7/2000 | Cundari et al. |
| 6,101,236 A | 8/2000 | Wang et al. |
| 6,102,866 A | 8/2000 | Nields et al. |
| 6,137,527 A | 10/2000 | Abdel-Malek |
| 6,141,398 A | 10/2000 | He |
| 6,149,301 A | 11/2000 | Kautzer et al. |
| 6,175,117 B1 | 1/2001 | Komardin |
| 6,196,715 B1 | 3/2001 | Nambu |
| 6,215,892 B1 | 4/2001 | Douglass et al. |
| 6,216,540 B1 | 4/2001 | Nelson |
| 6,219,059 B1 | 4/2001 | Argiro |
| 6,233,473 B1 | 5/2001 | Sheperd |
| 6,243,441 B1 | 6/2001 | Zur |
| 6,245,028 B1 | 6/2001 | Furst et al. |
| 6,256,370 B1 | 7/2001 | Yavus |
| 6,272,207 B1 | 8/2001 | Tang |
| 6,289,235 B1 | 9/2001 | Webber et al. |
| 6,292,530 B1 | 9/2001 | Yavus |
| 6,293,282 B1 | 9/2001 | Lemelson |
| 6,327,336 B1 | 12/2001 | Gingold et al. |
| 6,327,377 B1 | 12/2001 | Rutenberg et al. |
| 6,341,156 B1 | 1/2002 | Baetz |
| 6,375,352 B1 | 4/2002 | Hewes |
| 6,389,104 B1 | 5/2002 | Bani-Hashemi et al. |
| 6,411,836 B1 | 6/2002 | Patel |
| 6,415,015 B2 | 7/2002 | Nicolas |
| 6,424,332 B1 | 7/2002 | Powell |
| 6,442,288 B1 | 8/2002 | Haerer |
| 6,459,925 B1 | 10/2002 | Nields et al. |
| 6,463,181 B2 | 10/2002 | Duarte |
| 6,468,226 B1 | 10/2002 | McIntyre, IV |
| 6,480,565 B1 | 11/2002 | Ning |
| 6,501,819 B2 | 12/2002 | Unger et al. |
| 6,556,655 B1 | 4/2003 | Chichereau |
| 6,574,304 B1 | 6/2003 | Hsieh |
| 6,597,762 B1 | 7/2003 | Ferrant |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes |
| 6,638,235 B2 | 10/2003 | Miller et al. |

(56)                References Cited

U.S. PATENT DOCUMENTS

| | | |
|---|---|---|
| 6,647,092 B2 | 11/2003 | Eberhard |
| 6,650,928 B1 | 11/2003 | Gailly |
| 6,683,934 B1 | 1/2004 | Zhao |
| 6,744,848 B2 | 6/2004 | Stanton |
| 6,748,044 B2 | 6/2004 | Sabol et al. |
| 6,751,285 B2 | 6/2004 | Eberhard |
| 6,758,824 B1 | 7/2004 | Miller et al. |
| 6,813,334 B2 | 11/2004 | Koppe |
| 6,882,700 B2 | 4/2005 | Wang |
| 6,885,724 B2 | 4/2005 | Li |
| 6,901,156 B2 | 5/2005 | Giger et al. |
| 6,912,319 B1 | 6/2005 | Barnes |
| 6,940,943 B2 | 9/2005 | Claus |
| 6,978,040 B2 | 12/2005 | Berestov |
| 6,987,331 B2 | 1/2006 | Koeppe |
| 6,999,553 B2 | 2/2006 | Livingston |
| 6,999,554 B2 | 2/2006 | Mertelmeier |
| 7,022,075 B2 | 4/2006 | Grunwald et al. |
| 7,025,725 B2 | 4/2006 | Dione et al. |
| 7,030,861 B1 | 4/2006 | Westerman |
| 7,110,490 B2 | 9/2006 | Eberhard |
| 7,110,502 B2 | 9/2006 | Tsuji |
| 7,117,098 B1 | 10/2006 | Dunlay et al. |
| 7,123,684 B2 | 10/2006 | Jing et al. |
| 7,127,091 B2 | 10/2006 | OpDeBeek |
| 7,142,633 B2 | 11/2006 | Eberhard |
| 7,218,766 B2 | 5/2007 | Eberhard |
| 7,245,694 B2 | 7/2007 | Jing et al. |
| 7,286,634 B2 | 10/2007 | Sommer, Jr. et al. |
| 7,289,825 B2 | 10/2007 | Fors et al. |
| 7,298,881 B2 | 11/2007 | Giger et al. |
| 7,315,607 B2 | 1/2008 | Ramsauer |
| 7,319,735 B2 | 1/2008 | Defreitas et al. |
| 7,323,692 B2 | 1/2008 | Rowlands |
| 7,346,381 B2 | 3/2008 | Okerlund et al. |
| 7,406,150 B2 | 7/2008 | Minyard et al. |
| 7,430,272 B2 | 9/2008 | Jing et al. |
| 7,443,949 B2 | 10/2008 | Defreitas et al. |
| 7,466,795 B2 | 12/2008 | Eberhard et al. |
| 7,556,602 B2 | 7/2009 | Wang et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,630,533 B2 | 12/2009 | Ruth et al. |
| 7,634,050 B2 | 12/2009 | Muller et al. |
| 7,640,051 B2 | 12/2009 | Krishnan |
| 7,697,660 B2 | 4/2010 | Ning |
| 7,702,142 B2 | 4/2010 | Ren et al. |
| 7,705,830 B2 | 4/2010 | Westerman et al. |
| 7,760,924 B2 | 7/2010 | Ruth et al. |
| 7,769,219 B2 | 8/2010 | Zahniser |
| 7,787,936 B2 | 8/2010 | Kressy |
| 7,809,175 B2 | 10/2010 | Roehrig et al. |
| 7,828,733 B2 | 11/2010 | Zhang et al. |
| 7,831,296 B2 | 11/2010 | DeFreitas et al. |
| 7,869,563 B2 | 1/2011 | DeFreitas |
| 7,974,924 B2 | 7/2011 | Holla et al. |
| 7,991,106 B2 | 8/2011 | Ren et al. |
| 8,044,972 B2 | 10/2011 | Hall et al. |
| 8,051,386 B2 | 11/2011 | Rosander et al. |
| 8,126,226 B2 | 2/2012 | Bernard et al. |
| 8,155,421 B2 | 4/2012 | Ren et al. |
| 8,165,365 B2 | 4/2012 | Bernard et al. |
| 8,532,745 B2 | 9/2013 | DeFreitas et al. |
| 8,571,289 B2 | 10/2013 | Ruth |
| 8,594,274 B2 | 11/2013 | Hoernig et al. |
| 8,677,282 B2 | 3/2014 | Cragun et al. |
| 8,712,127 B2 | 4/2014 | Ren et al. |
| 8,787,522 B2 | 7/2014 | Smith et al. |
| 8,897,535 B2 | 11/2014 | Ruth et al. |
| 8,983,156 B2 | 3/2015 | Periaswamy et al. |
| 9,020,579 B2 | 4/2015 | Smith |
| 9,075,903 B2 | 7/2015 | Marshall |
| 9,084,579 B2 | 7/2015 | Ren et al. |
| 9,119,599 B2 | 9/2015 | Itai |
| 9,129,362 B2 | 9/2015 | Jerebko |
| 9,289,183 B2 | 3/2016 | Karssemeijer |
| 9,451,924 B2 | 9/2016 | Bernard |
| 9,456,797 B2 | 10/2016 | Ruth et al. |
| 9,478,028 B2 | 10/2016 | Parthasarathy |
| 9,589,374 B1 | 3/2017 | Gao |
| 9,592,019 B2 | 3/2017 | Sugiyama |
| 9,805,507 B2 | 10/2017 | Chen |
| 9,808,215 B2 | 11/2017 | Ruth et al. |
| 9,811,758 B2 | 11/2017 | Ren et al. |
| 9,901,309 B2 | 2/2018 | DeFreitas et al. |
| 10,008,184 B2 | 6/2018 | Kreeger et al. |
| 10,010,302 B2 | 7/2018 | Ruth et al. |
| 10,074,199 B2 | 9/2018 | Robinson et al. |
| 10,092,358 B2 | 10/2018 | DeFreitas |
| 10,111,631 B2 | 10/2018 | Gkanatsios |
| 10,242,490 B2 | 3/2019 | Karssemeijer |
| 10,276,265 B2 | 4/2019 | Reicher et al. |
| 10,282,840 B2 | 5/2019 | Moehrle et al. |
| 10,335,094 B2 | 7/2019 | DeFreitas |
| 10,357,211 B2 | 7/2019 | Smith |
| 10,410,417 B2 | 9/2019 | Chen et al. |
| 10,413,263 B2 | 9/2019 | Ruth et al. |
| 10,444,960 B2 | 10/2019 | Marshall |
| 10,456,213 B2 | 10/2019 | DeFreitas |
| 10,573,276 B2 | 2/2020 | Kreeger et al. |
| 10,575,807 B2* | 3/2020 | Gkanatsios ........... A61B 6/502 |
| 10,595,954 B2 | 3/2020 | DeFreitas |
| 10,624,598 B2 | 4/2020 | Chen |
| 10,977,863 B2 | 4/2021 | Chen |
| 10,978,026 B2 | 4/2021 | Kreeger |
| 11,419,565 B2* | 8/2022 | Gkanatsios ........... G06T 11/008 |
| 11,508,340 B2 | 11/2022 | Kreeger |
| 11,701,199 B2 | 7/2023 | DeFreitas |
| 2001/0038681 A1 | 11/2001 | Stanton et al. |
| 2001/0038861 A1 | 11/2001 | Hsu et al. |
| 2002/0012450 A1 | 1/2002 | Tsuji |
| 2002/0050986 A1 | 5/2002 | Inoue |
| 2002/0075997 A1 | 6/2002 | Unger et al. |
| 2002/0113681 A1 | 8/2002 | Byram |
| 2002/0122533 A1 | 9/2002 | Marie et al. |
| 2002/0188466 A1 | 12/2002 | Barrette et al. |
| 2002/0193676 A1 | 12/2002 | Bodicker |
| 2003/0007598 A1 | 1/2003 | Wang |
| 2003/0018272 A1 | 1/2003 | Treado et al. |
| 2003/0026386 A1 | 2/2003 | Tang |
| 2003/0048260 A1 | 3/2003 | Matusis |
| 2003/0073895 A1 | 4/2003 | Nields et al. |
| 2003/0095624 A1 | 5/2003 | Eberhard et al. |
| 2003/0097055 A1* | 5/2003 | Yanof ................... A61B 6/032 |
| | | 600/407 |
| 2003/0128893 A1 | 7/2003 | Castorina |
| 2003/0135115 A1 | 7/2003 | Burdette et al. |
| 2003/0169847 A1 | 9/2003 | Karellas |
| 2003/0194050 A1 | 10/2003 | Eberhard |
| 2003/0194121 A1 | 10/2003 | Eberhard et al. |
| 2003/0194124 A1 | 10/2003 | Suzuki et al. |
| 2003/0195433 A1 | 10/2003 | Turovskiy |
| 2003/0210254 A1 | 11/2003 | Doan |
| 2003/0212327 A1 | 11/2003 | Wang |
| 2003/0215120 A1 | 11/2003 | Uppaluri |
| 2004/0008809 A1 | 1/2004 | Webber |
| 2004/0008900 A1 | 1/2004 | Jabri et al. |
| 2004/0008901 A1 | 1/2004 | Avinash |
| 2004/0036680 A1 | 2/2004 | Davis |
| 2004/0047518 A1 | 3/2004 | Tiana |
| 2004/0052328 A1 | 3/2004 | Saboi |
| 2004/0064037 A1 | 4/2004 | Smith |
| 2004/0066884 A1 | 4/2004 | Claus |
| 2004/0066904 A1 | 4/2004 | Eberhard et al. |
| 2004/0070582 A1 | 4/2004 | Smith et al. |
| 2004/0077938 A1 | 4/2004 | Mark et al. |
| 2004/0081273 A1 | 4/2004 | Ning |
| 2004/0094167 A1 | 5/2004 | Brady |
| 2004/0101095 A1 | 5/2004 | Jing et al. |
| 2004/0109028 A1 | 6/2004 | Stern et al. |
| 2004/0109529 A1 | 6/2004 | Eberhard et al. |
| 2004/0127789 A1 | 7/2004 | Ogawa |
| 2004/0138569 A1 | 7/2004 | Grunwald |

(56)  References Cited

U.S. PATENT DOCUMENTS

| | | |
|---|---|---|
| 2004/0171933 A1 | 9/2004 | Stoller et al. |
| 2004/0171986 A1 | 9/2004 | Tremaglio, Jr. et al. |
| 2004/0267157 A1 | 12/2004 | Miller et al. |
| 2005/0047636 A1 | 3/2005 | Gines et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0084060 A1 | 4/2005 | Seppi et al. |
| 2005/0089205 A1 | 4/2005 | Kapur |
| 2005/0105679 A1 | 5/2005 | Wu et al. |
| 2005/0107689 A1 | 5/2005 | Sasano |
| 2005/0111718 A1 | 5/2005 | MacMahon |
| 2005/0113680 A1 | 5/2005 | Ikeda et al. |
| 2005/0113681 A1 | 5/2005 | DeFreitas et al. |
| 2005/0113715 A1 | 5/2005 | Schwindt et al. |
| 2005/0124845 A1 | 6/2005 | Thomadsen et al. |
| 2005/0135555 A1 | 6/2005 | Claus |
| 2005/0135664 A1 | 6/2005 | Kaufhold |
| 2005/0226375 A1 | 10/2005 | Eberhard |
| 2006/0004278 A1 | 1/2006 | Giger et al. |
| 2006/0009693 A1 | 1/2006 | Hanover et al. |
| 2006/0018526 A1 | 1/2006 | Avinash |
| 2006/0025680 A1 | 2/2006 | Jeune-Iomme |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0132508 A1 | 6/2006 | Sadikali |
| 2006/0147099 A1 | 7/2006 | Marshall et al. |
| 2006/0154267 A1 | 7/2006 | Ma et al. |
| 2006/0155209 A1 | 7/2006 | Miller et al. |
| 2006/0197753 A1 | 9/2006 | Hotelling |
| 2006/0210131 A1 | 9/2006 | Wheeler |
| 2006/0228012 A1 | 10/2006 | Masuzawa |
| 2006/0238546 A1 | 10/2006 | Handley |
| 2006/0257009 A1 | 11/2006 | Wang |
| 2006/0269040 A1 | 11/2006 | Mertelmeier |
| 2006/0274928 A1 | 12/2006 | Collins et al. |
| 2006/0291618 A1 | 12/2006 | Eberhard et al. |
| 2007/0014468 A1 | 1/2007 | Gines et al. |
| 2007/0019846 A1 | 1/2007 | Bullitt et al. |
| 2007/0030949 A1 | 2/2007 | Jing et al. |
| 2007/0036265 A1 | 2/2007 | Jing et al. |
| 2007/0046649 A1 | 3/2007 | Reiner |
| 2007/0047793 A1 | 3/2007 | Wu et al. |
| 2007/0052700 A1 | 3/2007 | Wheeler et al. |
| 2007/0076844 A1 | 4/2007 | Defreitas et al. |
| 2007/0114424 A1 | 5/2007 | Danielsson et al. |
| 2007/0118400 A1 | 5/2007 | Morita et al. |
| 2007/0156451 A1 | 7/2007 | Gering |
| 2007/0223651 A1 | 9/2007 | Wagenaar et al. |
| 2007/0225600 A1 | 9/2007 | Weibrecht et al. |
| 2007/0236490 A1 | 10/2007 | Casteele |
| 2007/0242800 A1 | 10/2007 | Jing et al. |
| 2007/0263765 A1 | 11/2007 | Wu |
| 2007/0274585 A1 | 11/2007 | Zhang et al. |
| 2008/0019581 A1 | 1/2008 | Gkanatsios et al. |
| 2008/0043905 A1 | 2/2008 | Hassanpourgol |
| 2008/0045833 A1 | 2/2008 | DeFreitas et al. |
| 2008/0101537 A1 | 5/2008 | Sendai |
| 2008/0114614 A1 | 5/2008 | Mahesh et al. |
| 2008/0125643 A1 | 5/2008 | Huisman |
| 2008/0130979 A1 | 6/2008 | Ren |
| 2008/0139896 A1 | 6/2008 | Baumgart |
| 2008/0152086 A1 | 6/2008 | Hall |
| 2008/0165136 A1 | 7/2008 | Christie et al. |
| 2008/0187095 A1 | 8/2008 | Boone et al. |
| 2008/0198966 A1 | 8/2008 | Hjarn |
| 2008/0221479 A1 | 9/2008 | Ritchie |
| 2008/0229256 A1 | 9/2008 | Shibaike |
| 2008/0240533 A1 | 10/2008 | Piron et al. |
| 2008/0297482 A1 | 12/2008 | Weiss |
| 2009/0003519 A1 | 1/2009 | DeFreitas |
| 2009/0005668 A1 | 1/2009 | West et al. |
| 2009/0005693 A1 | 1/2009 | Brauner |
| 2009/0010384 A1 | 1/2009 | Jing et al. |
| 2009/0034684 A1 | 2/2009 | Bernard |
| 2009/0037821 A1 | 2/2009 | O'Neal et al. |
| 2009/0063118 A1 | 3/2009 | Dachille et al. |
| 2009/0079705 A1 | 3/2009 | Sizelove et al. |
| 2009/0080594 A1 | 3/2009 | Brooks et al. |
| 2009/0080602 A1 | 3/2009 | Brooks et al. |
| 2009/0080604 A1 | 3/2009 | Shores et al. |
| 2009/0080752 A1* | 3/2009 | Ruth .......................... A61B 6/12 |
| | | 382/132 |
| 2009/0080765 A1 | 3/2009 | Bernard et al. |
| 2009/0087067 A1 | 4/2009 | Khorasani |
| 2009/0123052 A1 | 5/2009 | Ruth |
| 2009/0129644 A1 | 5/2009 | Daw et al. |
| 2009/0135997 A1 | 5/2009 | Defreitas et al. |
| 2009/0138280 A1 | 5/2009 | Morita et al. |
| 2009/0143674 A1 | 6/2009 | Nields |
| 2009/0167702 A1 | 7/2009 | Nurmi |
| 2009/0171244 A1 | 7/2009 | Ning |
| 2009/0238424 A1 | 9/2009 | Arakita |
| 2009/0259958 A1 | 10/2009 | Ban |
| 2009/0268865 A1 | 10/2009 | Ren et al. |
| 2009/0278812 A1 | 11/2009 | Yasutake |
| 2009/0296882 A1 | 12/2009 | Gkanatsios et al. |
| 2009/0304147 A1 | 12/2009 | Jing et al. |
| 2010/0034348 A1 | 2/2010 | Yu |
| 2010/0049046 A1 | 2/2010 | Peiffer |
| 2010/0054400 A1 | 3/2010 | Ren et al. |
| 2010/0067648 A1 | 3/2010 | Kojima |
| 2010/0079405 A1 | 4/2010 | Bernstein |
| 2010/0086188 A1 | 4/2010 | Ruth et al. |
| 2010/0088346 A1 | 4/2010 | Urness et al. |
| 2010/0098214 A1 | 4/2010 | Star-Lack et al. |
| 2010/0105879 A1 | 4/2010 | Katayose et al. |
| 2010/0119164 A1 | 5/2010 | Singhal |
| 2010/0121178 A1 | 5/2010 | Krishnan |
| 2010/0131294 A1 | 5/2010 | Venon |
| 2010/0131482 A1 | 5/2010 | Linthicum et al. |
| 2010/0131887 A1 | 5/2010 | Salazar-Ferrer |
| 2010/0135558 A1 | 6/2010 | Ruth et al. |
| 2010/0152570 A1 | 6/2010 | Navab |
| 2010/0166147 A1 | 7/2010 | Abenaim |
| 2010/0166267 A1 | 7/2010 | Zhang |
| 2010/0171764 A1 | 7/2010 | Feng et al. |
| 2010/0189322 A1 | 7/2010 | Sakagawa |
| 2010/0195882 A1 | 8/2010 | Ren et al. |
| 2010/0208037 A1 | 8/2010 | Sendai |
| 2010/0231522 A1 | 9/2010 | Li |
| 2010/0246884 A1 | 9/2010 | Chen et al. |
| 2010/0246909 A1 | 9/2010 | Blum |
| 2010/0259561 A1 | 10/2010 | Forutanpour et al. |
| 2010/0259645 A1 | 10/2010 | Kaplan |
| 2010/0260316 A1 | 10/2010 | Stein et al. |
| 2010/0280375 A1 | 11/2010 | Zhang |
| 2010/0293500 A1 | 11/2010 | Cragun |
| 2011/0018817 A1 | 1/2011 | Kryze |
| 2011/0019891 A1 | 1/2011 | Puong |
| 2011/0054944 A1 | 3/2011 | Sandberg et al. |
| 2011/0069808 A1 | 3/2011 | Defreitas et al. |
| 2011/0069906 A1 | 3/2011 | Park |
| 2011/0087132 A1 | 4/2011 | DeFreitas et al. |
| 2011/0105879 A1 | 5/2011 | Masumoto |
| 2011/0109650 A1* | 5/2011 | Kreeger .................. G16H 50/20 |
| | | 345/634 |
| 2011/0110570 A1 | 5/2011 | Bar-Shalev |
| 2011/0110576 A1 | 5/2011 | Kreeger |
| 2011/0123073 A1 | 5/2011 | Gustafson |
| 2011/0125526 A1 | 5/2011 | Gustafson |
| 2011/0134113 A1 | 6/2011 | Ma et al. |
| 2011/0150447 A1 | 6/2011 | Li |
| 2011/0157154 A1 | 6/2011 | Bernard et al. |
| 2011/0163939 A1 | 7/2011 | Tam et al. |
| 2011/0178389 A1 | 7/2011 | Kumar et al. |
| 2011/0182402 A1 | 7/2011 | Partain |
| 2011/0234630 A1 | 9/2011 | Batman et al. |
| 2011/0237927 A1 | 9/2011 | Brooks et al. |
| 2011/0242092 A1 | 10/2011 | Kashiwagi |
| 2011/0310126 A1 | 12/2011 | Georgiev et al. |
| 2012/0014501 A1 | 1/2012 | Pelc |

(56) References Cited

U.S. PATENT DOCUMENTS

| | | |
|---|---|---|
| 2012/0014504 A1 | 1/2012 | Jang |
| 2012/0014578 A1 | 1/2012 | Karssemeijer |
| 2012/0069951 A1 | 3/2012 | Toba |
| 2012/0106698 A1 | 5/2012 | Karim |
| 2012/0127297 A1 | 5/2012 | Baxi |
| 2012/0131488 A1 | 5/2012 | Karlsson et al. |
| 2012/0133600 A1 | 5/2012 | Marshall |
| 2012/0133601 A1 | 5/2012 | Marshall |
| 2012/0134464 A1 | 5/2012 | Hoernig et al. |
| 2012/0148151 A1 | 6/2012 | Hamada |
| 2012/0150034 A1 | 6/2012 | DeFreitas et al. |
| 2012/0189092 A1 | 7/2012 | Jerebko |
| 2012/0194425 A1* | 8/2012 | Buelow ............... G06T 19/00 |
| | | 345/156 |
| 2012/0238870 A1 | 9/2012 | Smith et al. |
| 2012/0277625 A1 | 11/2012 | Nakayama |
| 2012/0293511 A1 | 11/2012 | Mertelmeier |
| 2013/0016255 A1 | 1/2013 | Bhatt |
| 2013/0022165 A1 | 1/2013 | Jang |
| 2013/0023056 A1 | 1/2013 | Raftery |
| 2013/0044861 A1 | 2/2013 | Muller |
| 2013/0059758 A1 | 3/2013 | Haick |
| 2013/0108138 A1 | 5/2013 | Nakayama |
| 2013/0121569 A1 | 5/2013 | Yadav |
| 2013/0121618 A1 | 5/2013 | Yadav |
| 2013/0202168 A1 | 8/2013 | Jerebko |
| 2013/0259193 A1 | 10/2013 | Packard |
| 2013/0272494 A1 | 10/2013 | DeFreitas |
| 2014/0033126 A1* | 1/2014 | Kreeger ............. G06T 11/003 |
| | | 715/833 |
| 2014/0035811 A1 | 2/2014 | Guehring |
| 2014/0064444 A1 | 3/2014 | Oh |
| 2014/0073913 A1 | 3/2014 | DeFreitas et al. |
| 2014/0082542 A1 | 3/2014 | Zhang et al. |
| 2014/0200433 A1 | 7/2014 | Choi |
| 2014/0219534 A1 | 8/2014 | Wiemker et al. |
| 2014/0219548 A1 | 8/2014 | Wels |
| 2014/0276061 A1 | 9/2014 | Lee et al. |
| 2014/0327702 A1 | 11/2014 | Kreeger et al. |
| 2014/0328517 A1 | 11/2014 | Gluncic |
| 2015/0004558 A1 | 1/2015 | Inglese |
| 2015/0052471 A1 | 2/2015 | Chen |
| 2015/0061582 A1 | 3/2015 | Tatsuta et al. |
| 2015/0238148 A1 | 8/2015 | Georgescu |
| 2015/0258271 A1 | 9/2015 | Love |
| 2015/0302146 A1 | 10/2015 | Marshall |
| 2015/0309712 A1 | 10/2015 | Marshall |
| 2015/0317538 A1 | 11/2015 | Ren et al. |
| 2015/0331995 A1 | 11/2015 | Zhao |
| 2016/0000399 A1 | 1/2016 | Halmann et al. |
| 2016/0022364 A1 | 1/2016 | DeFreitas et al. |
| 2016/0051215 A1 | 2/2016 | Chen |
| 2016/0078645 A1 | 3/2016 | Abdurahman |
| 2016/0140749 A1 | 5/2016 | Erhard |
| 2016/0210774 A1 | 7/2016 | Wiskin et al. |
| 2016/0228034 A1 | 8/2016 | Gluncic |
| 2016/0235380 A1 | 8/2016 | Smith |
| 2016/0350933 A1 | 12/2016 | Schieke |
| 2016/0364526 A1 | 12/2016 | Reicher et al. |
| 2016/0367210 A1 | 12/2016 | Gkanatsios |
| 2017/0071562 A1 | 3/2017 | Suzuki |
| 2017/0132792 A1 | 5/2017 | Jerebko et al. |
| 2017/0202453 A1 | 7/2017 | Sekiguchi |
| 2017/0262737 A1 | 9/2017 | Rabinovich |
| 2018/0008220 A1 | 1/2018 | Boone et al. |
| 2018/0008236 A1 | 1/2018 | Venkataraman et al. |
| 2018/0047211 A1 | 2/2018 | Chen et al. |
| 2018/0109698 A1 | 4/2018 | Ramsay et al. |
| 2018/0132722 A1 | 5/2018 | Eggers et al. |
| 2018/0137385 A1 | 5/2018 | Ren |
| 2018/0144244 A1 | 5/2018 | Masoud |
| 2018/0256118 A1 | 9/2018 | DeFreitas |
| 2019/0000318 A1 | 1/2019 | Caluser |
| 2019/0015173 A1 | 1/2019 | DeFreitas |
| 2019/0037173 A1 | 1/2019 | Lee et al. |

| | | |
|---|---|---|
| 2019/0043456 A1 | 2/2019 | Kreeger |
| 2019/0057778 A1 | 2/2019 | Porter et al. |
| 2019/0287241 A1 | 9/2019 | Hill et al. |
| 2019/0290221 A1 | 9/2019 | Smith |
| 2019/0325573 A1 | 10/2019 | Bernard et al. |
| 2020/0046303 A1 | 2/2020 | DeFreitas |
| 2020/0054300 A1 | 2/2020 | Kreeger et al. |
| 2020/0093562 A1 | 3/2020 | DeFreitas |
| 2020/0184262 A1 | 6/2020 | Chui |
| 2020/0205928 A1 | 7/2020 | DeFreitas |
| 2020/0253573 A1 | 8/2020 | Gkanatsios |
| 2020/0345320 A1 | 11/2020 | Chen |
| 2020/0390404 A1 | 12/2020 | DeFreitas |
| 2021/0000553 A1 | 1/2021 | St. Pierre |
| 2021/0100518 A1 | 4/2021 | Chui |
| 2021/0100626 A1 | 4/2021 | St. Pierre |
| 2021/0113167 A1 | 4/2021 | Chui |
| 2021/0118199 A1 | 4/2021 | Chui |
| 2021/0174504 A1 | 6/2021 | Madabhushi |
| 2021/0212665 A1 | 7/2021 | Tsymbalenko |
| 2022/0005277 A1 | 1/2022 | Chen |
| 2022/0013089 A1 | 1/2022 | Kreeger |
| 2022/0036545 A1 | 2/2022 | St. Pierre |
| 2022/0192615 A1 | 6/2022 | Chui |
| 2022/0254023 A1 | 8/2022 | McKinney et al. |
| 2022/0386969 A1 | 12/2022 | Smith |
| 2023/0000467 A1 | 1/2023 | Shi |
| 2023/0008465 A1 | 1/2023 | Smith |
| 2023/0033601 A1 | 2/2023 | Chui |
| 2023/0038498 A1 | 2/2023 | Xu |
| 2023/0053489 A1 | 2/2023 | Kreeger |
| 2023/0054121 A1 | 2/2023 | Chui |
| 2023/0056692 A1 | 2/2023 | Gkanatsios |
| 2023/0082494 A1 | 3/2023 | Chui |
| 2023/0098305 A1 | 3/2023 | St. Pierre |
| 2023/0103969 A1 | 4/2023 | St. Pierre |
| 2023/0124481 A1 | 4/2023 | St. Pierre |
| 2023/0125385 A1 | 4/2023 | Solis |
| 2023/0225821 A1 | 7/2023 | DeFreitas |
| 2023/0230679 A1 | 7/2023 | Chen |
| 2023/0240785 A1 | 8/2023 | DeFreitas |
| 2023/0344453 A1 | 10/2023 | Yang |
| 2023/0394769 A1 | 12/2023 | Chen |
| 2024/0169958 A1 | 5/2024 | Kreeger |
| 2024/0315654 A1 | 9/2024 | Chui |
| 2024/0320827 A1 | 9/2024 | Chui |
| 2024/0338864 A1 | 10/2024 | Chui |
| 2024/0341698 A1 | 10/2024 | DeFreitas |
| 2025/0082292 A1 | 3/2025 | Chui |

FOREIGN PATENT DOCUMENTS

| | | |
|---|---|---|
| CN | 1846622 | 10/2006 |
| CN | 101066212 A | 11/2007 |
| CN | 102169530 A | 8/2011 |
| CN | 202161328 | 3/2012 |
| CN | 102429678 | 5/2012 |
| CN | 102473300 A | 5/2012 |
| CN | 105193447 | 12/2015 |
| CN | 106659468 A | 5/2017 |
| CN | 107440730 | 12/2017 |
| CN | 112561908 A | 3/2021 |
| DE | 102010009295 | 8/2011 |
| DE | 102011087127 | 5/2013 |
| EP | 775467 | 5/1997 |
| EP | 982001 | 3/2000 |
| EP | 1428473 | 6/2004 |
| EP | 2236085 | 6/2010 |
| EP | 2215600 | 8/2010 |
| EP | 2301432 | 3/2011 |
| EP | 2491863 | 8/2012 |
| EP | 1986548 | 1/2013 |
| EP | 2656789 | 10/2013 |
| EP | 2823464 | 1/2015 |
| EP | 2823765 | 1/2015 |
| EP | 2889743 | 7/2015 |
| EP | 3060132 | 4/2019 |
| JP | H09-35043 | 2/1997 |
| JP | H09-198490 | 7/1997 |

(56) References Cited

FOREIGN PATENT DOCUMENTS

| | | |
|---|---|---|
| JP | H09-238934 | 9/1997 |
| JP | H10-33523 | 2/1998 |
| JP | 2000-200340 | 7/2000 |
| JP | 2002-109510 | 4/2002 |
| JP | 2002-282248 | 10/2002 |
| JP | 2003-126073 | 5/2003 |
| JP | 2003-189179 | 7/2003 |
| JP | 2003-199737 | 7/2003 |
| JP | 2003-531516 | 10/2003 |
| JP | 2004254742 | 9/2004 |
| JP | 2005-110843 | 4/2005 |
| JP | 2005-522305 | 7/2005 |
| JP | 2005-227350 | 8/2005 |
| JP | 2005-322257 | 11/2005 |
| JP | 2006-519634 | 8/2006 |
| JP | 2006-312026 | 11/2006 |
| JP | 2007-130487 | 5/2007 |
| JP | 2007-216022 | 8/2007 |
| JP | 2007-325928 | 12/2007 |
| JP | 2007-330334 | 12/2007 |
| JP | 2007-536968 | 12/2007 |
| JP | 2008-068032 | 3/2008 |
| JP | 2008518684 | 6/2008 |
| JP | 2008-253401 | 10/2008 |
| JP | 2009-034503 | 2/2009 |
| JP | 2009-522005 | 6/2009 |
| JP | 2009-526618 | 7/2009 |
| JP | 2009-207545 | 9/2009 |
| JP | 2010-137004 | 6/2010 |
| JP | 2011-110175 A | 6/2011 |
| JP | 2012-011255 | 1/2012 |
| JP | 2012-501750 | 1/2012 |
| JP | 2012-061196 | 3/2012 |
| JP | 2013-530768 | 8/2013 |
| JP | 2013-244211 | 12/2013 |
| JP | 2014-507250 | 3/2014 |
| JP | 2014-534042 | 12/2014 |
| JP | 2015-506794 | 3/2015 |
| JP | 2015-144632 A | 8/2015 |
| JP | 2016-198197 | 12/2015 |
| JP | 2016059743 | 4/2016 |
| JP | 2017-000364 | 1/2017 |
| JP | 2017-056358 | 3/2017 |
| KR | 10-2015-0010515 | 1/2015 |
| KR | 10-2017-0062839 | 6/2017 |
| WO | 90/05485 | 5/1990 |
| WO | 93/17620 | 9/1993 |
| WO | 94/06352 | 3/1994 |
| WO | 1997/00649 | 1/1997 |
| WO | 1998/16903 | 4/1998 |
| WO | 00/51484 | 9/2000 |
| WO | 2003/020114 | 3/2003 |
| WO | 03/077202 | 9/2003 |
| WO | 2005051197 | 6/2005 |
| WO | 2005110230 | 11/2005 |
| WO | 2005112767 | 12/2005 |
| WO | 2006/055830 | 5/2006 |
| WO | 2006/058160 | 6/2006 |
| WO | 2007/095330 | 8/2007 |
| WO | 08/014670 | 2/2008 |
| WO | 2008047270 | 4/2008 |
| WO | 2008/050823 | 5/2008 |
| WO | 2008/054436 | 5/2008 |
| WO | 2009/026587 | 2/2009 |
| WO | 2010/028208 | 3/2010 |
| WO | 2010059920 | 5/2010 |
| WO | 2011008239 | 1/2011 |
| WO | 2011/043838 | 4/2011 |
| WO | 2011065950 | 6/2011 |
| WO | 2011073864 | 6/2011 |
| WO | 2011091300 | 7/2011 |
| WO | 2012/001572 | 1/2012 |
| WO | 2012/068373 | 5/2012 |
| WO | 2012063653 | 5/2012 |
| WO | 2012/112627 | 8/2012 |
| WO | 2012/122399 | 9/2012 |
| WO | 2013/001439 | 1/2013 |
| WO | 2013/035026 | 3/2013 |
| WO | 2013/078476 | 5/2013 |
| WO | 2013/123091 | 8/2013 |
| WO | 2013/136222 | 9/2013 |
| WO | 2014/080215 | 5/2014 |
| WO | 2014/149554 | 9/2014 |
| WO | 2014/207080 | 12/2014 |
| WO | 2015/061582 | 4/2015 |
| WO | 2015/066650 | 5/2015 |
| WO | 2015/130916 | 9/2015 |
| WO | 2016/103094 | 6/2016 |
| WO | 2016/184746 | 11/2016 |
| WO | 2016/206942 | 12/2016 |
| WO | 2018/183548 | 10/2018 |
| WO | 2018/183549 | 10/2018 |
| WO | 2018/183550 | 10/2018 |
| WO | 2018/236565 | 12/2018 |
| WO | 2019/032558 | 2/2019 |
| WO | 2019/091807 | 5/2019 |
| WO | 2021/021329 | 2/2021 |
| WO | 2021/168281 | 8/2021 |
| WO | 2021/195084 | 9/2021 |

OTHER PUBLICATIONS

Cho, N. et al., "Distinguishing Benign from Malignant Masses at Breast US: Combined US Elastography and Color Doppler US—Influence on Radiologist Accuracy", Radiology, 262(1): 80-90 (Jan. 2012).

Green, C. et al., "Deformable mapping using biochemical models to relate corresponding lesions in digital breast tomosynthesis and automated breast ultrasound images", Medical Image Analysis, 60: 1-18 (Nov. 2019).

Kim, Eun Sil, et al., "Significance of microvascular evaluation of ductal lesions on breast ultrasonography: Influence on diagnostic performance", Clinical Imaging, Elsevier, NY, vol. 51, Jun. 6, 2018, pp. 252-259.

Lee, E. et al., "Combination of Quantitative Parameters of Shear Wave Elastography and Superb Microvascular Imaging to Evaluate Breast Masses", Korean Journal of Radiology: Official Journal of the Korean Radiological Society, 21(9): 1045-1054 (Jan. 2020).

Love, Susan M., et al. "Anatomy of the nipple and breast ducts revisited", Cancer, American Cancer Society, Philadelphia, PA, vol. 101, No. 9, Sep. 20, 2004, pp. 1947-1957.

"Filtered Back Projection", (NYGREN), published May 8, 2007, URL: http://web.archive.org/web/19991010131715/http://www.owlnet.rice.edu/~elec539/Projects97/cult/node2.html, 2 pgs.

"Supersonic to feature Aixplorer Ultimate at ECR", AuntiMinnie.com, 3 pages (Feb. 2018).

Al Sallab et al., "Self Learning Machines Using Deep Networks", Soft Computing and Pattern Recognition (SoCPaR), 2011 Int'l. Conference of IEEE, Oct. 14, 2011, pp. 21-26.

Berg, WA et al., "Combined screening with ultrasound and mammography vs mammography alone in women at elevated risk of breast cancer", JAMA 299:2151-2163, 2008.

Burbank, Fred, "Stereotactic Breast Biopsy: Its History, Its Present, and Its Future", published in 1996 at the Southeastern Surgical Congress, 24 pages.

Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.

Caroline, B.E. et al., "Computer aided detection of masses in digital breast tomosynthesis: A review", 2012 International Conference on Emerging Trends in Science, Engineering and Technology (INCOSET), Tiruchirappalli, 2012, pp. 186-191.

Carton, AK, et al., "Dual-energy contrast-enhanced digital breast tomosynthesis—a feasibility study", Br J Radiol. Apr. 2010;83 (988):344-50.

Chan, Heang-Ping et al., "Computer-aided detection system for breast masses on digital tomosynthesis mammograms: Preliminary Experience", Radiology, Dec. 2005, 1075-1080.

(56) References Cited

OTHER PUBLICATIONS

Chan, Heang-Ping et al., "ROC Study of the effect of stereoscopic imaging on assessment of breast lesions," Medical Physics, vol. 32, No. 4, Apr. 2005, 1001-1009.

Chen, SC, et al., "Initial clinical experience with contrast-enhanced digital breast tomosynthesis", Acad Radio. Feb. 2007 14(2):229-38.

Conner, Peter, "Breast Response to Menopausal Hormone Therapy—Aspects on Proliferation, apoptosis and Mammographic Density", 2007 Annals of Medicine, 39;1, 28-41.

Diekmann, Felix et al., "Thick Slices from Tomosynthesis Data Sets: Phantom Study for the Evaluation of Different Algorithms", Journal of Digital Imaging, Springer, vol. 22, No. 5, Oct. 23, 2007, pp. 519-526.

Diekmann, Felix., et al., "Digital mammography using iodine-based contrast media: initial clinical experience with dynamic contrast medium enhancement", Invest Radiol 2005; 40:397-404.

Dromain C., et al., "Contrast enhanced spectral mammography: a multi-reader study", RSNA 2010, 96th Scientific Assembly and Scientific Meeting.

Dromain, C., et al., "Contrast-enhanced digital mammography", Eur J Radiol. 2009; 69:34-42.

Dromain, Clarisse et al., "Dual-energy contrast-enhanced digital mammography: initial clinical results", European Radiology, Sep. 14, 2010, vol. 21, pp. 565-574.

Dromain, Clarisse, et al., "Evaluation of tumor angiogenesis of breast carcinoma using contrast-enhanced digital mammography", AJR: 187, Nov. 2006, 16 pages.

Duan, Xiaoman et al., "Matching corresponding regions of interest on cranio-caudal and medio-lateral oblique view mammograms", IEEE Access, vol. 7, Mar. 25, 2019, pp. 31586-31597, XP011715754, DOI: 10.1109/Access.2019.2902854, retrieved on Mar. 20, 2019, abstract.

E. Shaw de Paredes et al., "Interventional Breast Procedure", published Sep./Oct. 1998 in Curr Probl Diagn Radiol, pp. 138-184.

EFilm Mobile HD by Merge Healthcare, web site: http://itunes.apple.com/bw/app/efilm-mobile-hd/id405261243?mt=8, accessed on Nov. 3, 2011 (2 pages).

EFilm Solutions, eFilm Workstation (tm) 3.4, website: http://estore.merge.com/na/estore/content.aspx?productID=405, accessed on Nov. 3, 2011 (2 pages).

Elbakri, Idris A. et al., "Automatic exposure control for a slot scanning full field digital mammography system", Med. Phys.; Sep. 2005; 32(9):2763-2770, Abstract only.

Ertas, M. et al., "2D versus 3D total variation minimization in digital breast tomosynthesis", 2015 IEEE International Conference on Imaging Systems and Techniques (IST), Macau, 2015, pp. 1-4.

European Search Report in Application 21168134.1, mailed Jun. 24, 2021, 7 pages.

Extended European Search Report mailed Oct. 23, 2018 for EP Application No. 18165965.7, Applicant Hologic, Inc.

Feng, Steve Si Jia, et al., "Clinical digital breast tomosynthesis system: Dosimetric Characterization", Radiology, Apr. 2012, 263(1); pp. 35-42.

First Examination Report in AU Patent App. 1064451, mailed Oct. 31, 2018.

Fischer Imaging Corp, Mammotest Plus manual on minimally invasive breast biopsy system, 2002, 8 pages.

Fischer Imaging Corporation, Installation Manual, MammoTest Family of Breast Biopsy Systems, 86683G, 86684G, P-55957-IM, Issue 1, Revision 3, Jul. 2005, 98 pages.

Fischer Imaging Corporation, Operator Manual, MammoTest Family of Breast Biopsy Systems, 86683G, 86684G, P-55956-OM, Issue 1, Revision 6, Sep. 2005, 258 pages.

Foreign Office Action for Japanese Patent Application No. 2019-066645 dated Jan. 24, 2020.

Foreign Official Action for JP Patent App. 2019-66645, mailed Jul. 1, 2020.

Freiherr, G., "Breast tomosynthesis trials show promise", Diagnostic Imaging—San Francisco 2005, V27; N4:42-48.

Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages. (Reference labeled D10 in 0020 Opposition).

Ghiassi, M. et al., "A Dynamic Architecture for Artificial Networks", Neurocomputing, vol. 63, Aug. 20, 2004, pp. 397-413.

Giger et al. "Development of a smart workstation for use in mammography", in Proceedings of SPIE, vol. 1445 (1991), pp. 101103; 4 pages.

Giger et al., "An Intelligent Workstation for Computer-aided Diagnosis", in RadioGraphics, May 1993, 13:3 pp. 647-656; 10 pages.

Glick, Stephen J., "Breast CT", Annual Rev. Biomed. Eng., 2007, 9;501-26.

Hologic, "Lorad StereoLoc II" Operator's Manual 9-500-0261, Rev. 005, 2004, 78 pgs.

Hologic, Inc., 510(k) Summary, prepared Nov. 28, 2010, for Affirm Breast Biopsy Guidance System Special 510(k) Premarket Notification, 5 pages.

Hologic, Inc., 510(k) Summary, prepared Aug. 14, 2012, for Affirm Breast Biopsy Guidance System Special 510(k) Premarket Notification, 5 pages.

ICRP Publication 60: 1990 Recommendations of the International Commission on Radiological Protection, 12 pages.

Ijaz, Umer Zeeshan, et al., "Mammography phantom studies using 3D electrical impedance tomography with numerical forward solver", Frontiers in the Convergence of Bioscience and Information Technologies 2007, 379-383.

Japanese Decision of Refusal in Application 20.19-066645, mailed Apr. 2, 2021, 4 pages.

Japanese Decision to Grant in Application 2016-549766, mailed Mar. 14, 2019, 5 pages.

Japanese Refusal and Search Report in Application 2016-549766, mailed Oct. 11, 2018, 38 pages.

Japanese Refusal and Search Report in Application 2019-066645, mailed Jan. 24, 2020, 31 pages.

Japanese Refusal and Search Report in Application 2019-066645, mailed Jul. 1, 2020, 10 pages.

Jochelson, M., et al, "Bilateral Dual Energy contrast-enhanced digital mammography: Initial Experience", RSNA 2010, 96th Scientific Assembly and Scientific Meeting, 1 page.

Jong, RA, et al., Contrast-enhanced digital mammography: initial clinical experience. Radiology 2003; 228:842-850.

Kao, Tzu-Jen et al., "Regional admittivity spectra with tomosynthesis images for breast cancer detection", Proc. of the 29th Annual Int'l. Conf. of the IEEE EMBS, Aug. 23-26, 2007, 4142-4145.

Koechli, Ossi R., "Available Stereotactic Systems for Breast Biopsy", Renzo Brun del Re (Ed.), Minimally Invasive Breast Biopsies, Recent Results in Cancer Research 173:105-113; Springer-Verlag, 2009.

Kopans, Daniel B., "Breast Imaging", 3rd Edition, Lippincott Williams and Wilkins, published Nov. 2, 2006, pp. 960-967.

Kopans, et. al. Will tomosynthesis replace conventional mammography? Plenary Session SFN08: RSNA 2005.

Korean Reason for Refusal in Application I0-2016-7023205, mailed Sep. 17, 2021, 13 pages.

Lehman, CD, et al. MRI evaluation of the contralateral breast in women with recently diagnosed breast cancer. N Engl J Med 2007; 356:1295-1303.

Lewin, JM, et al., Dual-energy contrast-enhanced digital subtraction mammography: feasibility. Radiology 2003; 229:261-268.

Lilja, Mikko, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway, NJ, Oct. 25, 2008.

Lindfors, KK, et al., Dedicated breast CT: initial clinical experience. Radiology 2008; 246(3): 725-733.

Mahesh, Mahadevappa, "AAPM/RSNA Physics Tutorial for Residents—Digital Mammography: An Overview", Nov.-Dec. 2004, vol. 24, No. 6, 1747-1760.

Metheany, Kathrine G. et al., "Characterizing anatomical variability in breast CT images", Oct. 2008, Med. Phys. 35 (10); 4685-4694.

(56)          References Cited

OTHER PUBLICATIONS

Niklason, L., et al., Digital tomosynthesis in breast imaging. Radiology. Nov. 1997; 205(2):399-406.

Nikunjc, Oza et al., Dietterich, T.G., Ed., "Ensemble methods in machine learning", Jan. 1, 2005, Multiple Classifier Systems, Lecture Notes in Computer Science; LNCS, Springer-Verlag Berlin/ Heidelberg, pp. 1-15, abstract.

Notification of the First Office action for Chinese application No. 201580010642.2 dated Feb. 11, 2018, applicant Hologic Inc., English language translation from Chinese associate (7 pages).

Notification of the Second Office action for Chinese application No. 201580010642.2 dated Apr. 26, 2019, applicant Hologic Inc., in Chinese with English language translation from Chinese associate (12 pages).

PCT International Preliminary Report on Patentability in Application PCT/US2015/017713, rnaiied May 9, 2016, 7 pages.

PCT International Search Report and Written Opinion mailed May 15, 2015 for PCT/US2015/017713, Applicant Hologic, Inc., international filing date Feb. 26, 2015, 10 pages.

Pediconi, "Color-coded automated signal intensity-curve for detection and characterization of breast lesions: Preliminary evaluation of new software for MR-based breast imaging," International Congress Series 1281 (2005) 1081-1086.

Poplack, SP, et al., Digital breast tomosynthesis: initial experience in 98 women with abnormal digital screening mammography. AJR Am J Roentgenology Sep. 2007 189(3):616-23.

Prionas, ND, et al., Contrast-enhanced dedicated breast CT: initial clinical experience. Radiology. Sep. 2010 256(3):714-723.

Rafferty, E. et al., "Assessing Radiologist Performance Using Combined Full-Field Digital Mammography and Breast Tomosynthesis Versus Full-Field Digital Mammography Alone: Results" . . . presented at 2007 Radiological Society of North America meeting, Chicago IL.

Reynolds, April, "Stereotactic Breast Biopsy: A Review", Radiologic Technology, vol. 80, No. 5, Jun. 1, 2009, pp. 447M-464M, XP055790574.

Sakic et al., "Mammogram synthesis using a 3D simulation. I. breast tissue model and image acquisition simulation" Medical Physics. 29, pp. 2131-2139 (2002).

Samani, A. et al., "Biomechanical 3-D Finite Element Modeling of the Human Breast Using MRI Data", 2001, IEEE Transactions on Medical Imaging, vol. 20, No. 4, pp. 271-279.

Samulski, Maurice et al., "Optimizing case-based detection performance in a multiview CAD system for mammography", IEEE Transactions on Medical Imaging, vol. 30, No. 4, Apr. 1, 2011, pp. 1001-1009, XP011352387, ISSN: 0278-0062, DOI: 10.1109/TMI. 2011.2105886, abstract.

Sechopoulos, et al., "Glandular radiation dose in tomosynthesis of the breast using tungsten targets", Journal of Applied Clinical Medical Physics, vol. 8, No. 4, Fall 2008, 161-171.

Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.

Smith, A., "Full field breast tomosynthesis", Radiol Manage. Sep.-Oct. 2005; 27(5):25-31.

Taghibakhsh, f. et al., "High dynamic range 2-TFT amplified pixel sensor architecture for digital mammography tomosynthesis", IET Circuits Devices Syst., 2007, 1(10, pp. 87-92.

Van Schie, Guido, et al., "Generating Synthetic Mammograms from Reconstructed Tomosynthesis Volumes", IEEE Transactions on Medical Imaging, vol. 32, No. 12, Dec. 2013, 2322-2331.

Van Schie, Guido, et al., "Mass detection in reconstructed digital breast tomosynthesis volumes with a computer-aided detection system trained on 2D mammograms", Med. Phys. 40(4), Apr. 2013, 41902-1-41902-11.

Varjonen, Mari, "Three-Dimensional Digital Breast Tomosynthesis in the Early Diagnosis and Detection of Breast Cancer", IWDM 2006, LNCS 4046, 152-159.

Weidner N, et al., "Tumor angiogenesis and metastasis: correlation in invasive breast carcinoma", New England Journal of Medicine 1991; 324:1-8.

Weidner, N, "The importance of tumor angiogenesis: the evidence continues to grow", AM J Clin Pathol. Nov. 2004 122(5):696-703.

Wen, Junhai et al., "A study on truncated cone-beam sampling strategies for 3D mammography", 2004, IEEE, 3200-3204.

Williams, Mark B. et al., "Optimization of exposure parameters in full field digital mammography", Medical Physics 35, 2414 (May 20, 2008); doi: 10.1118/1.2912177, pp. 2414-2423.

Wodajo, Felasfa, MD, "Now Playing: Radiology Images from Your Hospital PACS on your iPad," Mar. 17, 2010; web site: http://www. imedicalapps.com/2010/03/now-playing-radiology-images-from-your-hospital-pacs-on-your-ipad/, accessed on Nov. 3, 2011 (3 pages).

Yin, H.M., et al., "Image Parser: a tool for finite element generation from three-dimensional medical images", BioMedical Engineering Online. 3:31, pp. 1-9, Oct. 1, 2004.

Zhang, Yiheng et al., "A comparative study of limited-angle cone-beam reconstruction methods for breast tomosynthesis", Med Phys., Oct. 2006, 33(10): 3781-3795.

Zhao, Bo, et al., "Imaging performance of an amorphous selenium digital mammography detector in a breast tomosynthesis system", May 2008, Med. Phys 35(5); 1978-1987.

* cited by examiner

60

62

64

66

68

70

72

74

76

Start

Acquire image Data set

Select Merge Mode (optional)

Map Images to Common coordinate system

Apply image filters

For Each Region $R_{0,0} \rightarrow R_{n,n}$

Compare region pixel values $I_{MERGE}$(Region) = ImageSet (Image(Region)) with highest value No All Regions Evaluated?

Finish

SYSTEM AND METHOD FOR GENERATING AND DISPLAYING TOMOSYNTHESIS IMAGE SLABS

RELATED APPLICATIONS DATA

This patent application is a continuation of U.S. patent application Ser. No. 17/869,408, now U.S. Pat. No. 11,801, 025, filed Jul. 20, 2022, which is a continuation of U.S. patent application Ser. No. 16/792,127, now U.S. Pat. No. 11,419,565, filed Feb. 14, 2020, which is a continuation of U.S. patent application Ser. No. 16/143,181, now U.S. Pat. No. 10,575,807, filed Sep. 26, 2018, which is a continuation of U.S. patent application Ser. No. 15/120,911, now U.S. Pat. No. 10,111,631, filed Aug. 23, 2016, which is a National Phase entry under 35 U.S.C § 371 of International Patent Application No. PCT/US2015/017713, having an international filing date of Feb. 26, 2015, which claims the benefit under 35 U.S.C. § 119 to U.S. Provisional Patent Application Ser. No. 61/946,417, filed Feb. 28, 2014, which are incorporated by reference in their entireties into the present application.

FIELD

The present disclosure relates generally to breast imaging using tomosynthesis, and more specifically to systems and methods for obtaining, processing, synthesizing, storing and displaying a tomosynthesis data set or a subset thereof. In particular, the present disclosure relates to generating and displaying 2D image slabs by importing relevant data from a subset of reconstructed tomosynthesis image slices of a data set into the synthesized images.

BACKGROUND

Mammography has long been used to screen for breast cancer and other abnormalities. Traditionally, mammograms have been formed on x-ray film. More recently, flat panel digital imagers have been introduced that acquire a mammogram in digital form, and thereby facilitate analysis and storage of the acquired image data, and to also provide other benefits. Further, substantial attention and technological development have been dedicated to obtaining three-dimensional images of the breast using methods such as breast tomosynthesis. In contrast to the 2D images generated by legacy mammography systems, breast tomosynthesis systems construct a 3D image volume from a series of 2D projection images, each projection image obtained at a different angular displacement of an x-ray source relative to the image detector as the x-ray source is scanned over the detector. The constructed 3D image volume is typically presented as a plurality of slices of image data, the slices being mathematically reconstructed on planes typically parallel to the imaging detector. The reconstructed tomosynthesis slices reduce or eliminate the problems caused by tissue overlap and structure noise present in single slice, two-dimensional mammography imaging, by permitting a user (e.g., a radiologist or other medical professional) to scroll through the image slices to view only the structures in that slice.

Tomosynthesis systems have recently been developed for breast cancer screening and diagnosis. In particular, Hologic, Inc. (www.hologic.com) has developed a fused, multimode mammography/tomosynthesis system that acquires one or both types of mammogram and tomosynthesis images, either while the breast remains immobilized or in different compressions of the breast. Other companies have proposed the introduction of systems which are dedicated to tomosynthesis imaging; i.e., which do not include the ability to also acquire a mammogram in the same compression.

Examples of systems and methods that leverage existing medical expertise in order to facilitate, optionally, the transition to tomosynthesis technology are described in U.S. Pat. No. 7,760,924, which is hereby incorporated by reference in its entirety. In particular, U.S. Pat. No. 7,760,924 describes a method of generating a synthesized 2D image, which may be displayed along with tomosynthesis projection or reconstructed images, in order to assist in screening and diagnosis.

While a 2D image synthesized from the entire tomosynthesis data set provides a useful overview of the image data that is similar to a traditional mammography image, a single 2D image may contain too much data to facilitate optimal screening and diagnosis. Accordingly, there exists a need for tomosynthesis systems and methods for more effectively processing, synthesizing and displaying tomosynthesis image data.

SUMMARY

In accordance with various embodiments, a system for processing breast tissue images includes an image processing computer, and a user interface operatively coupled to the image processing computer, wherein the image processing computer is configured to obtain image data of breast tissue, processing the image data to generate a set of reconstructed image slices, the reconstructed image slices collectively depicting the breast tissue, process respective subsets of the reconstructed image slices to generate a set of image slabs, each image slab comprising a synthesized 2D image of a portion of the breast tissue obtained from a respective subset of the set of reconstructed image slices. The system may further comprise at least one image display monitor, wherein the image processing computer is further configured to cause to be displayed on a same or different display monitor of the one or more display monitors one or more image slabs of the generated set of image slabs. In various embodiments, the image processing computer is further configured to generate a storage file comprising the generated set of image slabs.

In one embodiment, the image processing computer is configured to generate each image slab of the set from a predetermined number of successive reconstructed image slices, wherein adjacent image slabs of the set include a predetermined overlap number of successive reconstructed image slices. In another embodiment, the image processing computer is configured to generate each image slab of the set from a user inputted number of successive reconstructed image slices, wherein adjacent image slabs of the set include a user inputted overlap number of successive reconstructed image slices. In one embodiment, respective slabs are generated from six successive image slabs, and wherein adjacent image slabs of the set include an overlap of three successive reconstructed image slices.

In various embodiments, the image slabs are generated using an enhancement mechanism that is selected or modified based on a number of reconstructed image slices from which the respective image slab is generated. By way of non-limiting example, the enhancement mechanism may be selected or modified based on a value corresponding to the number of reconstructed image slices from which the respective image slab is generated. By way of another non-limiting example, the enhancement mechanism may comprise highlighting one or more objects or regions in one or more image slabs of the set. In various embodiments, the enhancement mechanism takes into account one or more of: (i) a binary map of the respective highlighted objects or regions; (ii) a map of each image slice that includes a probability distribution for an identified pattern in the respective highlighted objects or regions; and (iii) importing an identified object or region from an image slice of the respective subset of reconstructed images slices into the image slab, wherein the object or region is imported into the image slab at X, Y coordinate locations corresponding to X, Y coordinate locations of the object or region in the respective reconstructed image slice.

In another embodiment of the disclosed inventions, a method for processing breast tissue image data includes obtaining image data of breast tissue, processing the image data to generate a set of reconstructed image slices, the reconstructed image slices collectively depicting the breast tissue, and processing respective subsets of the reconstructed image slices to generate a set of image slabs, each image slab of the set including a synthesized 2D image of a portion of the breast tissue obtained from a respective subset of the set of reconstructed image slices. In some embodiments, the slabs are generated from a predetermined number of successive image slices, and successive image slabs are generated from a predetermined overlap of image slices. In other embodiments, the slabs are generated from a user inputted number of successive image slices, and successive image slabs may be generated from a user inputted overlap of image slices. In one embodiment, respective slabs are generated from six successive image slabs, and wherein adjacent image slabs of the set include an overlap of three successive reconstructed image slices.

In various embodiments, the image slabs are generated using an enhancement mechanism (i.e., an image processing/synthesis function) that is selected or modified based on a number of reconstructed image slices from which the respective image slab is generated. The enhancement mechanism may be selected or modified based on a previously determined value corresponding to the number of reconstructed image slices from which the respective image slab is generated. The enhancement mechanism may be selected or modified based on a value determined based upon the number of reconstructed image slices from which the respective image slab is generated. The enhancement mechanism may include highlighting object(s) and/or regions in the respective image slabs. The enhancement mechanism may take into account a binary map of the object or region. The enhancement mechanism may take into account a map of each reconstructed image slice that includes a probability distribution for an identified pattern in the object or region. The enhancement mechanism may include importing an identified object or region from a reconstructed image slice of the respective subset into the image slab. By way of non-limiting example, the object(s) or region(s) may be imported into the image slab at X, Y coordinate locations corresponding to X, Y coordinate locations of the respective object(s) or region(s) in the respective reconstructed image slice(s).

In yet another embodiment, a method for processing breast tissue image data includes (i) obtaining image data of breast tissue, (ii) processing the image data to generate a set of reconstructed image slices collectively depicting the breast tissue, (iii) displaying a plurality of reconstructed image slices to a user, (iv) receiving user input identifying an image slice of the set, and (v) processing a subset of the image slices to generate an image slab comprising a synthesized 2D image of a portion of the breast tissue obtained from the subset of reconstructed image slices including the user-identified image slice. By way of non-limiting example, the slab may be generated from a user inputted number of successive image slices. The method may also include processing respective subsets of the reconstructed image slices to generate a user-inputted number of image slabs, each image slab including a synthesized 2D image of a portion of the breast tissue obtained from the respective subset of reconstructed image slices, and wherein successive image slabs of the plurality are generated from a user inputted overlap of reconstructed image slices.

These and other aspects and embodiments of the disclosed inventions are described in more detail below, in conjunction with the accompanying figures.

BRIEF DESCRIPTION OF FIGURES

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

DETAILED DESCRIPTION OF THE ILLUSTRATED EMBODIMENTS

Figure 1:
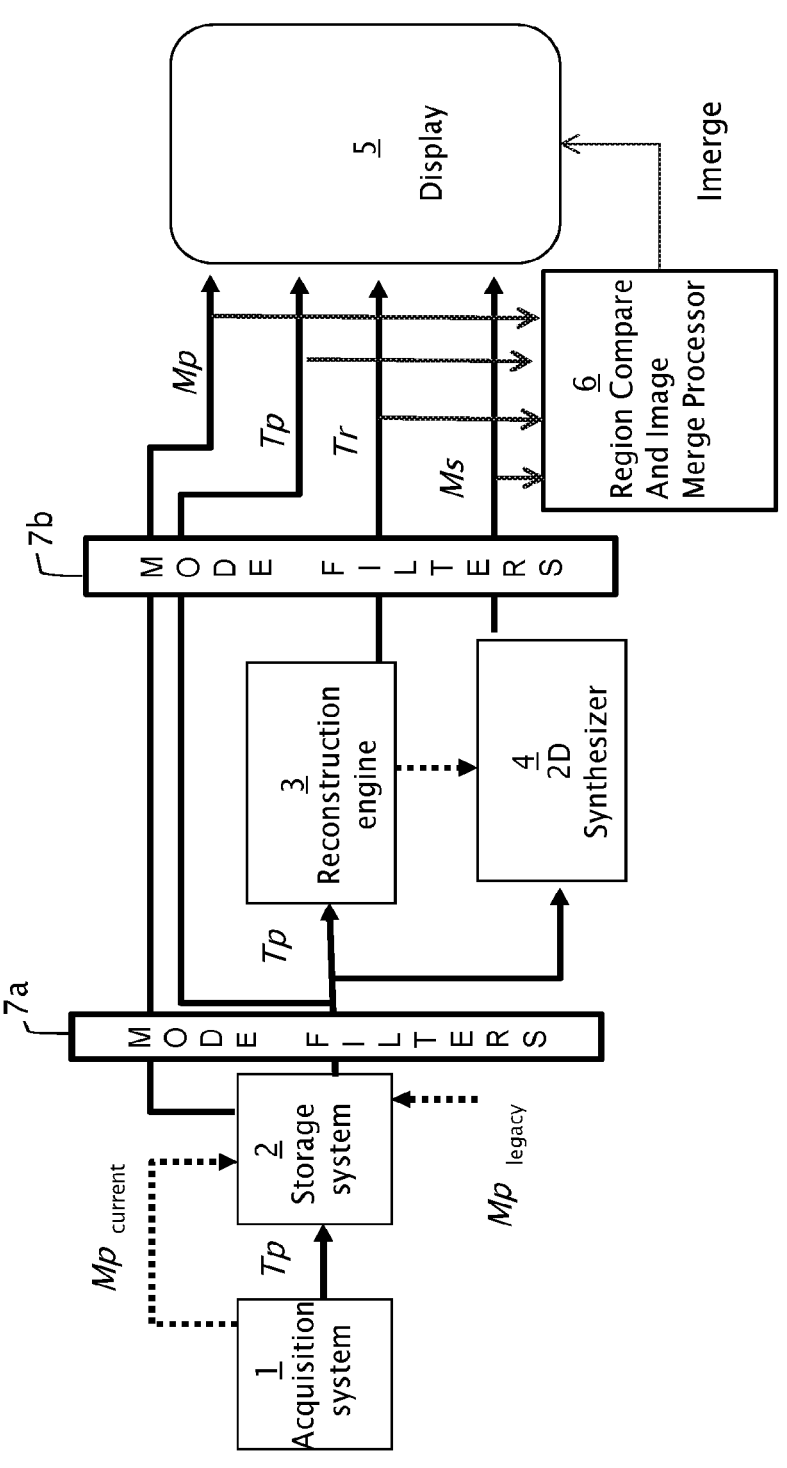
FIG. 1 is a block diagram illustrating the flow of data through a system that includes a combination mammography/tomosynthesis acquisition system and/or a tomosynthesis-only acquisition system to acquire tomosynthesis and/or mammography (including contrast mammography) images of a female breast, and further includes one or more processors that implement the image merge technology of the disclosed inventions for providing a two dimensional synthesized image by importing the most relevant data from the acquired 2D and/or 3D source images into one or more merged 2D images for display to a user (e.g., a medical professional, including a radiologist)

All numeric values are herein assumed to be modified by the terms "about" or "approximately," whether or not explicitly indicated. The terms "about" and "approximately" generally refers to a range of numbers that one of ordinary skill in the art would consider equivalent to the recited value (i.e., having the same function or result). In many instances, the terms "about" and "approximately" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. In describing the depicted embodiments of the disclosed inventions illustrated in the accompanying figures, specific terminology is employed for the sake of clarity and ease of description. However, the disclosure of this patent specification is not intended to be limited to the specific terminology so selected, and it is to be understood that each specific element includes all technical equivalents that operate in a similar manner. It is to be further understood that the various elements and/or features of different illustrative embodiments may be combined with each other and/or substituted for each other wherever possible within the scope of this disclosure and the appended claims.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the disclosed inventions, which is defined only by the appended claims and their equivalents. In addition, an illustrated embodiment of the disclosed inventions needs not have all the aspects or advantages shown. An aspect, feature or advantage described in conjunction with a particular embodiment of the disclosed inventions is not necessarily limited to that embodiment and can be practiced in any other embodiments even if not so illustrated.

For the following defined terms and abbreviations, these definitions shall be applied throughout this patent specification and the accompanying claims, unless a different definition is given in the claims or elsewhere in this specification:

Acquired image refers to an image generated while visualizing a woman's breast tissue. Acquired images can be generated by radiation from a radiation source impacting on a radiation detector disposed on opposite sides of the breast tissue, as in a conventional mammogram.

Reconstructed image refers to an image generated from data derived from a plurality of acquired images. A reconstructed image simulates an acquired image not included in the plurality of acquired images.

Synthesized image refers to an artificial image generated from data derived from a plurality of acquired and/or reconstructed images. A synthesized image includes elements (e.g., objects and regions) from the acquired and/or reconstructed images, but does not necessarily correspond to an image that can be acquired during visualization. Synthesized images are constructed analysis tools.

Mp refers to a conventional mammogram or contrast enhanced mammogram, which are two-dimensional (2D) projection images of a breast, and encompasses both a digital image as acquired by a flat panel detector or another imaging device, and the image after conventional processing to prepare it for display (e.g., to a health professional), storage (e.g., in the PACS system of a hospital), and/or other use.

Tp refers to an image that is similarly two-dimensional (2D), but is acquired at a respective tomosynthesis angle between the breast and the origin of the imaging x rays (typically the focal spot of an x-ray tube), and encompasses the image as acquired, as well as the image data after being processed for display, storage, and/or other use.

Tr refers to an image that is reconstructed from tomosynthesis projection images Tp, for example, in the manner described in one or more of U.S. Pat. Nos. 7,577,282, 7,606,801, 7,760,924, and 8,571,289, the respective disclosures of which are fully incorporated by reference herein in their entirety, wherein a Tr image represents a slice of the breast as it would appear in a projection x ray image of that slice at any desired angle, not only at an angle used for acquiring Tp or Mp images.

Ms refers to a synthesized 2D projection image, which simulates mammography images, such as a craniocaudal (CC) or mediolateral oblique (MLO) images, and is constructed using tomosynthesis projection images Tp, tomosynthesis reconstructed images Tr, or a combination thereof. Ms images may be provided for display to a health professional or for storage in the PACS system of a hospital or another institution. Examples of methods that may be used to generate Ms images are described in the above-referenced U.S. Pat. Nos. 7,760,924 and 8,571,289.

$I_{MERGE}$ refers to a synthesized 2D image constructed by importing into a single image one or more objects and/or regions from any two or more of Mp, Ms, Tp or Tr images of a woman's breast, wherein an image from which an object or region is imported into the merged image comprises a source image for that object or region, and wherein objects or regions are imported into the merged image at X, Y coordinate locations corresponding to the X, Y coordinate locations of the objects or regions in their respective source image. Examples of methods that may be used to generate $I_{MERGE}$ images are described in PCT Application Nos. PCT/US2012/066526 and PCT/US2013/025993, the respective disclosures of which are fully incorporated by reference herein in their entirety.

The terms $I_{MERGE}$, Tp, Tr, Ms and Mp each encompasses information, in whatever form, that is sufficient to describe the respective image for display, further processing, or storage. The respective $I_{MERGE}$, Mp, Ms. Tp and Tr images are typically provided in digital form prior to being displayed, with each image being defined by information that identifies the properties of each pixel in a two-dimensional array of pixels. The pixel values typically relate to respective measured, estimated, or computed responses to X-rays of corresponding volumes in the breast, i.e., voxels or columns of tissue. In one embodiment, the geometry of the tomosynthesis images (Tr and Tp), mammography images (Ms and Mp) and merged images ($I_{MERGE}$) are matched to a common coordinate system, as described in U.S. Pat. No. 7,702,142, the disclosure of which is hereby incorporated by reference in its entirety. Unless otherwise specified, such coordinate system matching is assumed to be implemented with respect to the embodiments described in the ensuing detailed description of this patent specification.

The terms "generating an image" and "transmitting an image" respectively refer to generating and transmitting information that is sufficient to describe the image for display. The generated and transmitted information is typically digital information.

FIG. 1 illustrates the flow of data in an exemplary image generation and display system, which incorporates merged image generation and display technology. It should be understood that, while FIG. 1 illustrates a particular embodiment of a flow diagram with certain processes taking place in a particular serial order or in parallel, the claims and various other embodiments are not limited to the performance of the image processing steps in any particular order, unless so specified.

More particularly, the image generation and display system includes an image acquisition system 1 that acquires tomosynthesis image data for generating Tp images of a woman's breast(s), using the respective three dimensional and/or tomosynthesis acquisition methods of any of the currently available systems. If the acquisition system is a combined tomosynthesis/mammography system, Mp images may also be generated. Some dedicated tomosynthesis systems or combined tomosynthesis/mammography systems may be adapted to accept and store legacy mammogram images, (indicated by a dashed line and legend Mp$_{legacy}$ in FIG. 1) in a storage device 2, which is preferably a DICOM-compliant Picture Archiving and Communication System (PACS) storage device. Following acquisition, the tomosynthesis projection images Tp may also be transmitted to the storage device 2 (as shown in FIG. 1).

The Tp images are transmitted from either the acquisition system 1, or from the storage device 2, or both, to a computer system configured as a reconstruction engine 3 that reconstructs the Tp images into reconstructed image "slices" Tr, representing breast slices of selected thickness and at selected orientations, as described in the above-referenced patents and applications. The imaging and display system 1 further includes a 2D synthesizer 4 that operates substantially in parallel with the reconstruction engine 3 for generating 2D images that simulate mammograms taken at any orientation (e.g., CC or MLO) using a combination of one or more Tp and/or Tr images. The synthesized 2D images may be generated dynamically prior to display (as shown in FIG. 1) or may be stored in storage system 2 for later use. The synthesized 2D images are interchangeably referenced as $I_{MERGE}$, T2d and Ms. The reconstruction engine 3 and 2D synthesizer 4 are preferably connected to a display system 5 via a fast transmission link.

The originally acquired Mp and/or Tp images may also be forwarded to the display system 5 for concurrent or toggled viewing with the respective $I_{MERGE}$, Tr, and/or Ms images by a user.

Mode filters 7a, 7b are disposed between image acquisition and image display. Each of the filters 7a and 7b may additionally include customized filters for each type of image (i.e., Tp, Mp, and Tr) arranged to identify and highlight certain aspects of the respective image types. In this manner, each imaging mode can be tuned or configured in an optimal way for a specific purpose. The tuning or configuration may be automatic, based on the type of the image, or may be defined by manual input, for example through a user interface coupled to a display. In the illustrated embodiment of FIG. 1, the filters 7a and 7b are selected to highlight particular characteristics of the images that are best displayed in respective imaging modes, for example, geared towards highlighting masses or calcifications, or for making the merged images (described below) appear to be a particular image type, such as a 3D reconstructed slice, or a 2D mammogram.

According to one embodiment of the disclosed inventions, and as described in greater detail herein, the system 1 includes an image merge processor 6 that merges relevant image data obtained from a set of available source and synthesized images of a woman's breast(s) to provide one or more merged 2D images ("slab" or $I_{MERGE}$) for display. The set of available images used to generate the merged images ("slab" or $I_{MERGE}$) may include filtered and/or unfiltered Ms, Mp, Tr and/or Tp images. While FIG. 1 depicts all these types of images being input into the image merge processor 6, it is also envisioned within the scope of the disclosed inventions that the merged images may be manually configurable. For example, a user interface or preset configuration may be provided and configured to allow a user to select a particular group of two or more images or image types for generating a synthesized 2D image "slab" or $I_{MERGE}$ for display.

By way of illustration, a user, such as a radiologist or other medical professional, may wish to merge two or more reconstructed tomosynthesis slices (Tr) in order to provide a merged image showing the most readily discerned structures in the collective tomosynthesis image data in a displayed synthesized 2D image ("slab" or $I_{MERGE}$), which essentially maps the tomosynthesis slices at a pixel wise granularity. Additionally or alternatively, the user may combine a 2D mammogram image, whether Mp or Ms, with a 3D projection (Tp), or with selected reconstructed images (Tr), in order to obtain a customized merged image ("slab" or $I_{MERGE}$) that highlights both calcifications and various tissue structures in the breast. Filters applied to each type of image can further highlight the types of structures or features in a merged image that are generally most prevalent or most readily discerned in the respective source image type. Thus, one type of filter may be applied to mammography images to highlight calcifications, while a different filter may be applied to tomosynthesis slices to highlight masses, allowing both the highlighted calcifications and highlighted tissue masses to be displayed in a single merged image. Filters may also provide a merged image with a desired look and feel; i.e., to make a merged image appear more like a tomosynthesis or mammography image.

The display system 5 may be part of a standard acquisition workstation (e.g., of acquisition system 1), or of a standard (multi-display) review station (not shown) that is physically remote from the acquisition system 1. In some embodiments, a display connected via a communication network may be used, for example, a display of a personal computer or of a so-called tablet, smart phone or other hand-held device. In any event, the display 5 of the system is preferably able to display $I_{MERGE}$, Ms, Mp, Tr, and/or Tp images concurrently, e.g., in separate side-by-side monitors of a review workstation, although the invention may still be implemented with a single display monitor, by toggling between images.

To facilitate the detection/diagnosis process, Tr slices are preferably reconstructed all to the same size for display, which can be the same as the size of an Mp or Ms image of the breast, or they can be initially reconstructed to sizes determined by the fan shape of the x ray beam used in the acquisition, and then later converted to that same size by appropriate interpolation and/or extrapolation. In this manner, images of different types and from different sources can be displayed in desirable size and resolution. For example, an image can be displayed in (1) Fit To View Port mode, in which the size of the displayed image size is maximized such that the entire imaged breast tissue is visible, (2) True Size mode, in which a display pixel on the screen corresponds to a pixel of the image, or (3) Right Size mode, in which the size of a displayed image is adjusted so that it matches that of another image being concurrently displayed, or with which the displayed image is, or can be, toggled.

For example, if two images of the same breast are taken and are not the same size, or do not have the same resolution, provisions may be made to automatically or user-selectively increase or reduce the magnification (i.e., "zoom in" or "zoom out") of one or both images, such that they appear to be the same size when they are concurrently displayed, or as a user toggles between the images. Known interpolation, extrapolation and/or weighting techniques can be used to accomplish the re-sizing process, and known image processing technology can also be used to make other characteristics of the displayed images similar in a way that facilitates detection/diagnosis. When viewing such resized images, according to one embodiment of the disclosed inventions, the merged images ("slab" or $I_{MERGE}$) are automatically resized, accordingly.

Thus, the system 1, which is described as for purposes of illustration and not limitation in this patent specification, is capable of receiving and selectively displaying tomosynthesis projection images Tp, tomosynthesis reconstruction images Tr, synthesized mammogram images Ms, and/or mammogram (including contrast mammogram) images Mp, or any one or sub combination of these image types. The system 1 employs software to convert (i.e., reconstruct) tomosynthesis images Tp into images Tr, software for synthesizing mammogram images Ms, and software for merging a set of images to provide a set of merged images ("slabs" or $I_{MERGE}$) each of which displays, for every region of the merged image, the most relevant feature in that region among all images in the source image set. For the purpose of this patent specification, an object of interest or feature in a source image may be considered a 'most relevant' feature for inclusion in a merged image based upon the application of one or more CAD algorithms to the collective source images, wherein the CAD algorithms assign numerical values, weights or thresholds, to pixels or regions of the respective source images based upon identified/detected objects and features of interest within the respective region or between features or, in instances when the merged images are generated directly from the synthesized image without CAD assistance, simply the pixel value, weight or other threshold associated with a pixel or region of the image. The objects and features of interest may include, for example, spiculated lesions, calcifications, and the like. Various systems and methods are currently well known for computerized detection of abnormalities in radiographic images, such as those described by Giger et al. in RadioGraphics, May 1993, pp. 647-656; Giger et al. in Proceedings of SPIE, Vol. 1445 (1991), pp. 101-103; and U.S. Pat. Nos. 4,907,156, 5,133,020, 5,343,390, and 5,491,627, each of which being hereby incorporated by reference in its entirety.

Figure 2:
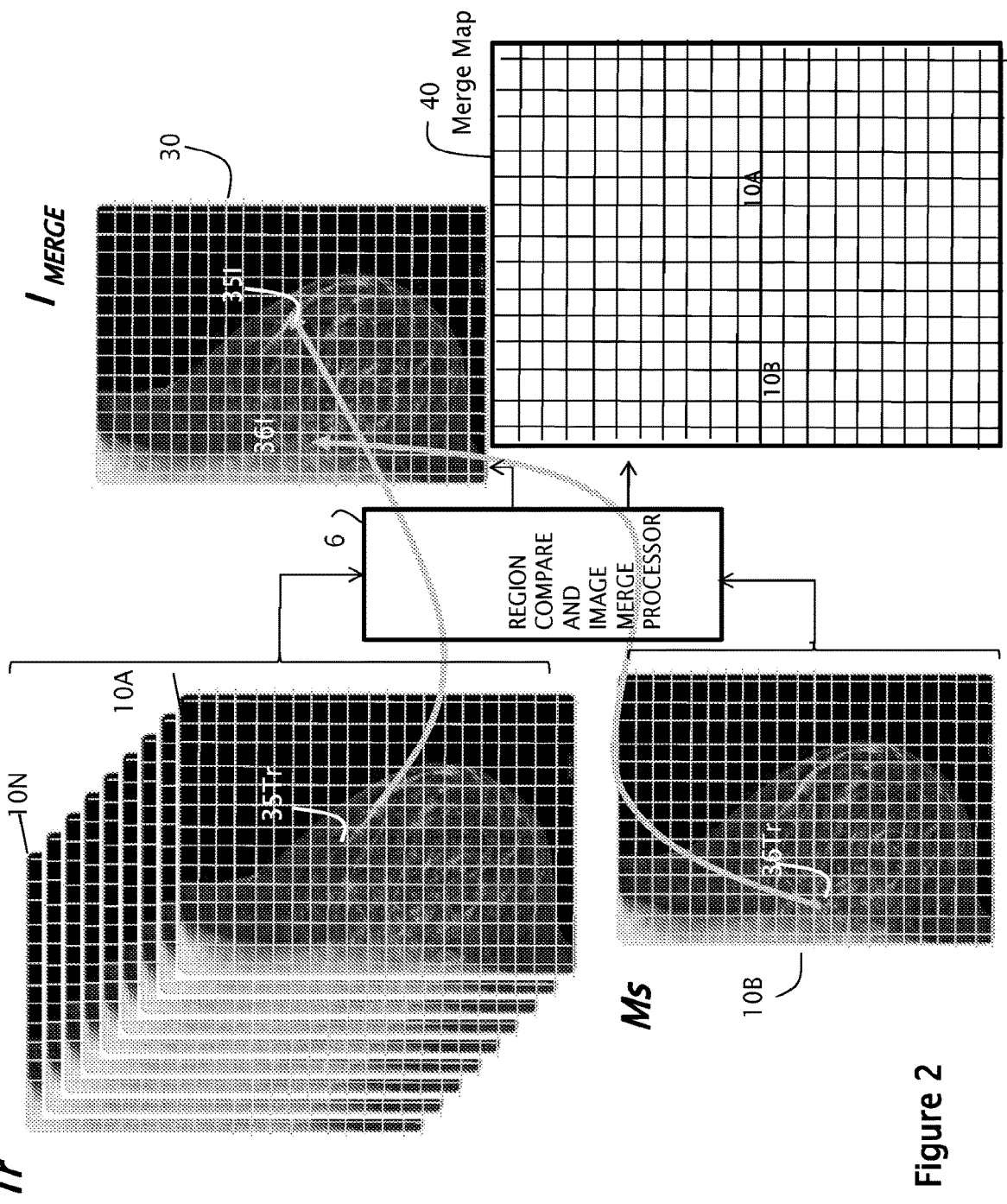
FIG. 2 is a diagram illustrating the data flow of a series of reconstructed Tr slices through the image merge technology of the disclosed inventions to generate a synthesized $I_{MERGE}$ image slab and a corresponding merge ("index" or "guidance") map.

FIG. 2 is a diagram which pictorially illustrates the merging of image data from a set of tomosynthesis reconstruction images (Tr), comprising tomosynthesis slices 10A to 10N, to generate a synthetic merged image ("slab" or $I_{MERGE}$) 30. For ease of description, filters are not shown in this example. The tomosynthesis image data set (Tr) are forwarded to the region compare and image merge processor 6, which evaluates each of the source images 10A-10N for which a plurality of merged images is to be generated (i.e., whether automatically, or based on a specific user command) in order to (1) identify the objects and features of interest in each image for those that may be considered a 'most relevant' feature for possible inclusion in one or more merged images 30 based upon the application of one or more CAD algorithms (as described above), (2) identifies respective pixel regions in the images 10A-10N that contain the identified features, and (3) thereafter compares the images on a region by region basis, searching for that image 10A-10N with the most desirable display data for each respective region.

As discussed above, the image 10A-10N with the most desirable display data may be an image with a highest pixel value, a lowest pixel value, or which has been assigned a threshold value or weight based on the application of a CAD algorithm to the image 10A-10N. When the image 10A-10N with the most desirable display data for that region is identified, the pixels of that region are copied over to the corresponding region of the one or more merged image 30. For example, as shown in FIG. 2, region 35Tr of tomosynthesis slice 10A is copied to region 35I of a merged image 30. In a similar manner, region 36Tr of tomosynthesis slice 10B is copied to region 36I of the merged image 30. Optionally, the region compare and image merge processor 6 can generate an index map 40 identifying the source images 10A, 10B of the objects 35I, 36I in the merged image 30. Although the regions of FIG. 2 are shown as pre-defined grid regions, it is not necessary that regions be pre-defined in this manner. Rather, according to one embodiment of the disclosed inventions, the boundaries of the regions may be dynamically identified during the region compare and image generation process by performing comparisons at pixel or multi-pixel granularities.

Figure 9:
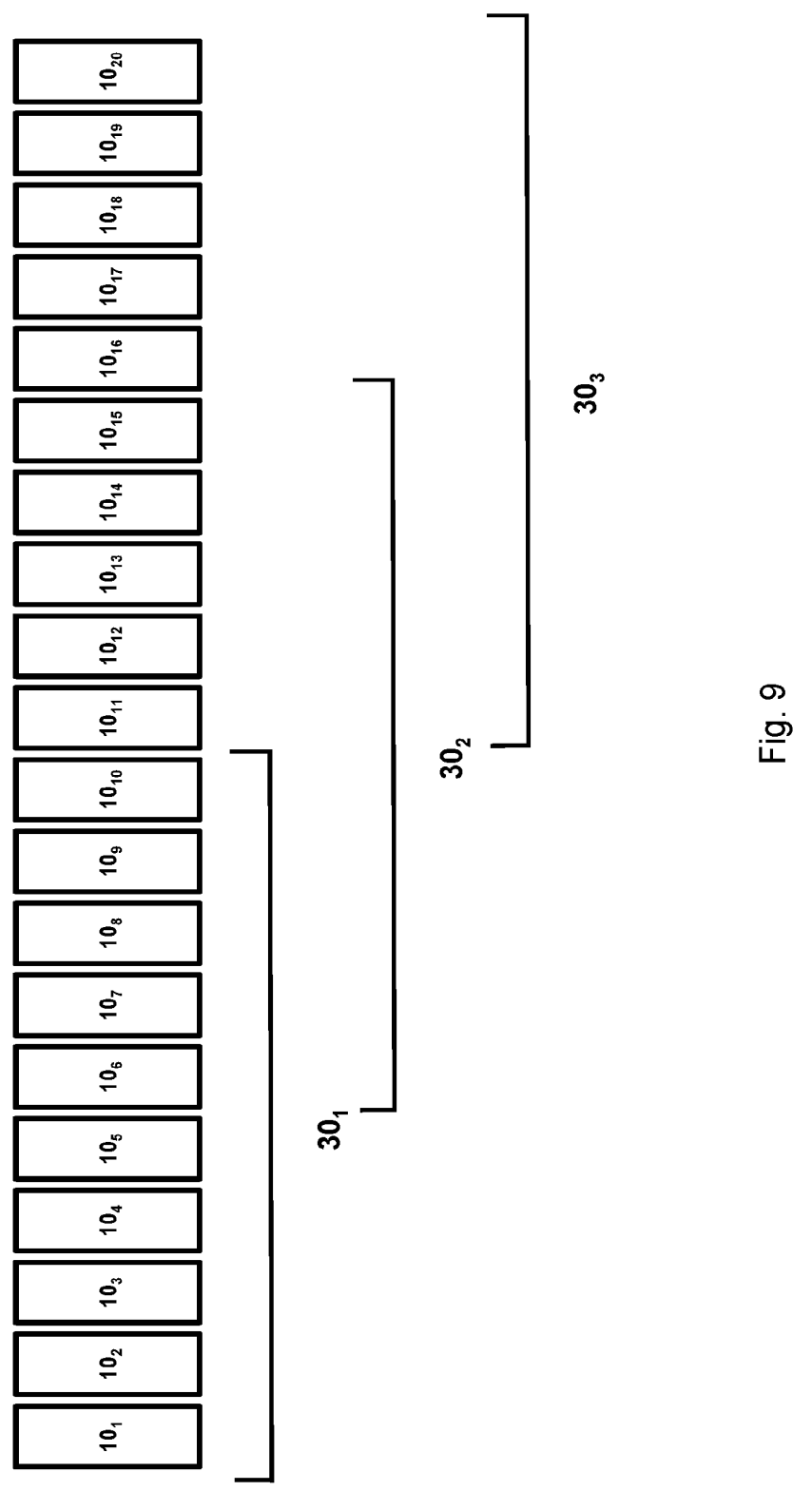
FIG. 9 is a diagram illustrating the data flow of a series of reconstructed Tr slices through the image merge technology of the disclosed inventions to generate a plurality of synthesized $I_{MERGE}$ image slabs.

In the embodiment shown in FIG. 9, a plurality of merged images ("slabs" or $I_{MERGE}$) 30 are synthesized from a set or stack of reconstructed Tr images ("slices") 10. For instance, 11 merged image slabs 30 are generated from a stack including 60 reconstructed Tr slices $10_1$-$10_{60}$, which is divided into 11 overlapping subsets of Tr slices 10 (only slices $10_1$-$10_{20}$ and slabs $30_1$-$30_3$ are shown for clarity). The first merged image slab $30_1$ is synthesized from Tr slices $10_1$-$10_{10}$, the second merged image slab $30_2$ is synthesized from Tr slices $10_6$-$10_{15}$, the third merged image slab $30_3$ is synthesized from Tr slices $10_{11}$-$10_{20}$, etc. This pattern is repeated until the eleventh merged image slab $30_{11}$ is synthesized from Tr slices $10_{51}$-$10_{60}$. In this embodiment, the default pattern of merged image slabs 30 includes a 10 slice thickness (i.e., N=10 in FIG. 2) with a 5 slice overlap between adjacent slabs 30. For a stack having a number of Tr slices 10 not divisible by 10, the merged image slabs 30 at one end of the stack can have a different number of Tr slices 10 per slab 30 and/or a different overlap with the adjacent slab 30.

While the foregoing described embodiment has a specific default pattern of merged image slabs 30, the invention encompasses any number of Tr slices 10 per slab 30, any amount of overlap between adjacent slabs 30, and any size stack. By way of non-limiting examples: in one embodiment, there are six Tr slices 10 per slab 30, with a with a three slice overlap between adjacent slabs. In another embodiment, there are eight Tr slices per slab 30, with a four slice overlap between adjacent slabs. In still another embodiment, there are fifteen Tr slices 10 per slab 30, with a ten slice overlap between adjacent slabs. In particular, the amount of overlapping Tr slices 10 in adjacent slabs 30 need not be exactly or approximately half of the respective slab size, but can be any number of Tr slices 10 selected by the operator.

In another embodiment, the system may display a user interface configured to receive input from a user. The user input may include a number of Tr slices 10 per slab 30, an amount of overlap between adjacent slabs 30, and a stack size. The system generates the plurality of slabs 30 based on the user input. In yet another embodiment with a user interface, the user input may include a Tr slice number (e.g., $10_{26}$) and a number of slices (e.g., five), and the system then generates a single slab 30 based on this user input. The slab 30 is generated from a subset of Tr slices 10 centered on the Tr slice corresponding to the user provided Tr slice number with the provided number of slices on each side of the center Tr slice (e.g., $10_{20}$-$10_{31}$). While two types of user input have been described, other types of user input are encompassed by the claims.

In still further embodiments, the number of Tr slices 10 per slab 30, the amount of overlap between adjacent slabs 30, and/or the respective stack size are preset values, and the slabs are automatically generated according to the preset values without requiring user input. In some such "automapping" embodiments, it may still be possible for the user to override any of the preset slab size, slice overlap amount, and stack size values.

Figure 3:
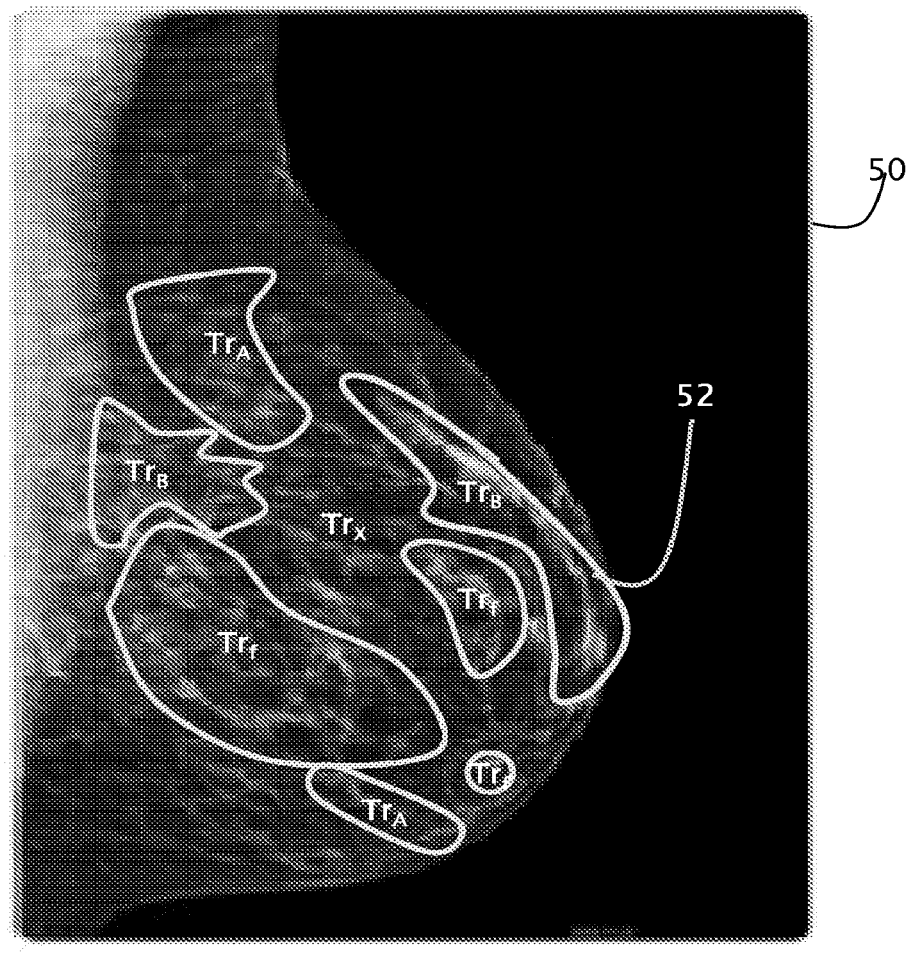
FIG. 3 depicts one embodiment of a displayed merged image, wherein certain region boundaries are dynamically identified during merge image build.

FIG. 3 illustrates a merged image 50, which has been constructed via the combinations of numerous regions 52 of different source images (Tr tomosynthesis slices $Tr_A$, $Tr_B$, $Tr_f$ and $Tr_X$), at arbitrary region boundaries, for example, which may be identified according to the detection of particular features within the respective source images $Tr_A$, $Tr_B$, $Tr_f$ and $Tr_X$. While the merged images 30 and 50 depicted in FIGS. 2 and 3 are generated from tomosynthesis reconstruction images or "slices" (Tr), merged images can be generated from tomosynthesis projection images Tp, tomosynthesis reconstruction images Tr, synthesized mammogram images Ms, and/or mammogram (including contrast mammogram) images Mp.

Figure 4:
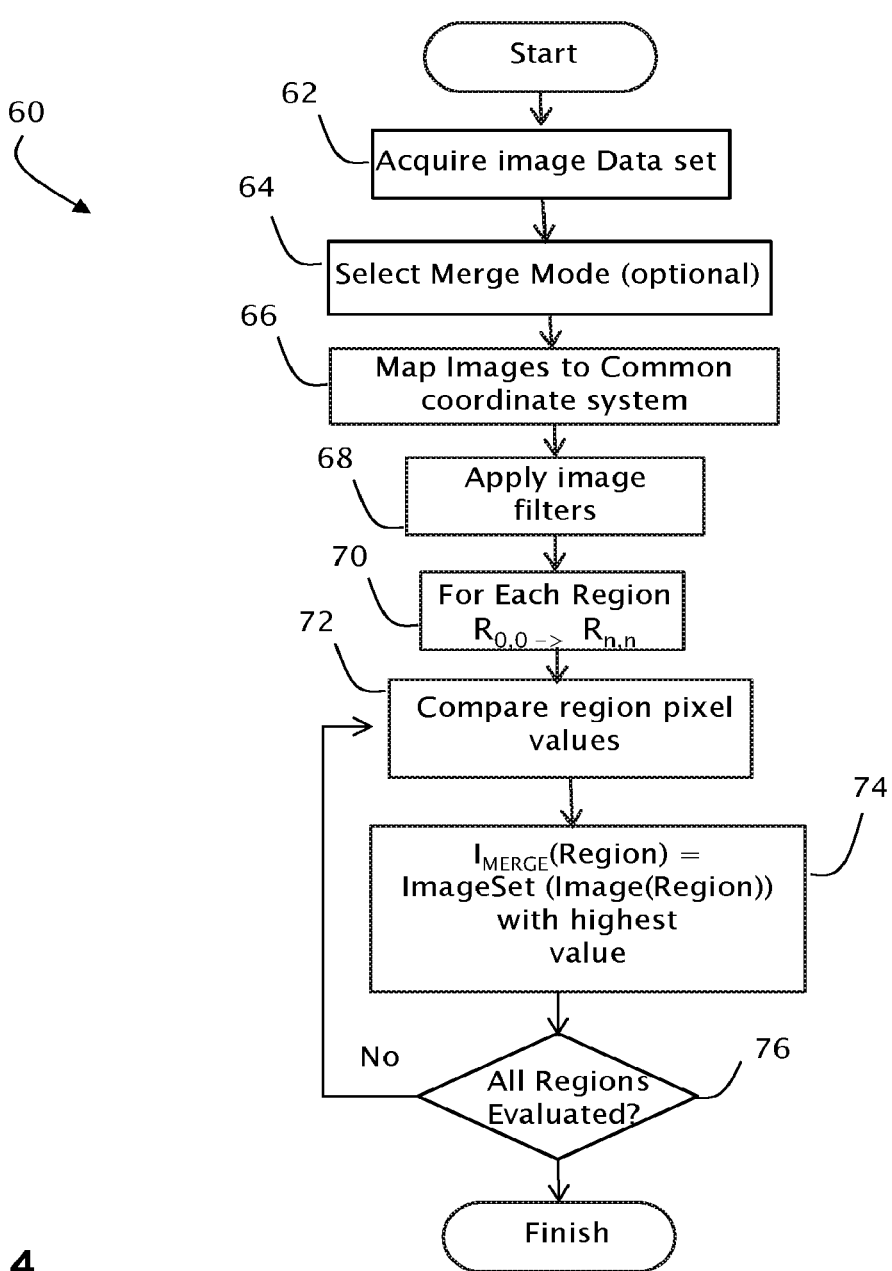
FIG. 4 is a flow diagram illustrating exemplary steps performed during an image merge process according to one embodiment of the disclosed inventions.

FIG. 4 is a flow diagram provided to illustrate exemplary steps that may be performed in an image merge process carried out in accordance with one embodiment of the disclosed inventions. At step 62, an image data set is acquired. The image data set may be acquired by a tomosynthesis acquisition system, a combination tomosynthesis/ mammography system, or by retrieving pre-existing image data from a storage device, whether locally or remotely located relative to an image display device. At step 64, a user may optionally select a merge mode, wherein the user may designate (1) which images are to be used for the source image set to generate one or more merged images, (2) whether to highlight certain features in the merged images, such as calcifications, spiculated lesions or masses, and (3) whether to display the image as a lower resolution tomosynthesis image, etc. At step 66, the images that are to be merged to generate the merged images are mapped to a common coordinate system, for example, as described in the above-referenced U.S. Pat. No. 7,702,142. Other methods of matching images of different coordinate systems may alternatively be used. At step 72, the process of comparing regions among the different images begins. At step 74, each $I_{MERGE}$ region is populated with the pixels of the region of an image from the source image set having the most desirable pixels, value, or pattern. The process of populating regions continues until it is determined, at step 76, that all regions have been evaluated, at which point the merged images are ready for display.

Figure 5A:
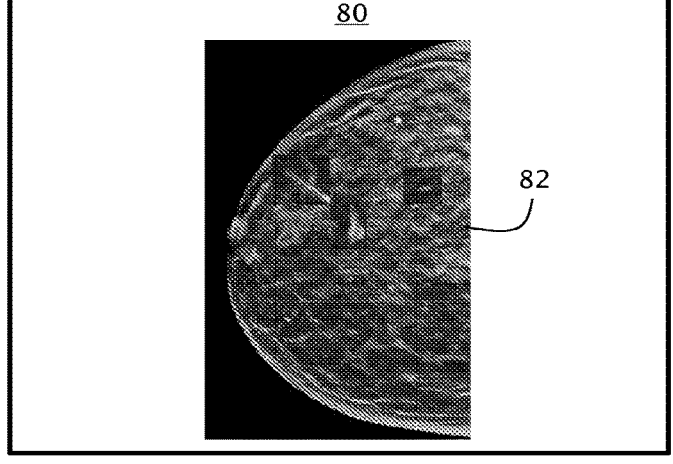
FIGS. 5A and 5B illustrate one embodiment of a display of a merged image, and a resultant display of a source image in response to selection of a region in the merged image by a user.
Figure 5B:
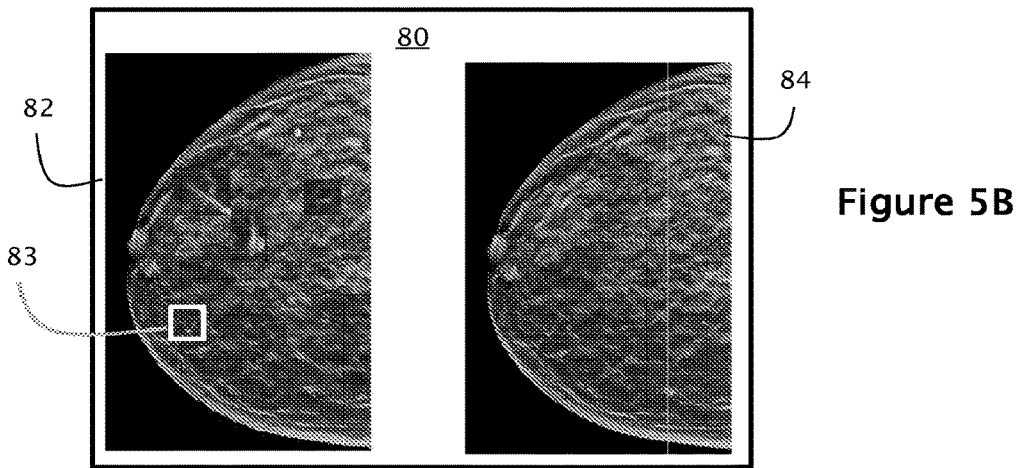

Once the merged images are generated, they may be used to assist in the navigation through a tomosynthesis image data stack from which the merge image was generated. Such navigation is a two-step process comprising selection of various objects of interest, and display of corresponding tomosynthesis images that are the source of such objects of interest in one or more of the merged images. By way of example, FIG. 5A and FIG. 5B illustrate two views of a display 80. The first view of display 80 shown in FIG. 5A illustrates a merged image 82, having regions sourced by different ones of an acquired or synthesized image set. FIG. 5B illustrates a particular feature enabled by the disclosed inventions, whereby a user may select a region or area 83 within the merged image 82, and the resulting image source 84 for that area is presented to the user.

The disclosed embodiments may employ many different mechanisms for selection of the objects of interest and corresponding display of the respective source images corresponding; although it is to be understood that the disclosed inventions are not limited to those described herein. For example, the selection of a region or area within a merged image may include a selection of a CAD mark, or alternatively a selection of a particular feature of interest to the reviewer. Navigating tomosynthesis image data using a merged image is detailed in the above-referenced PCT Application Nos. PCT/US2012/066526 and PCT/US2013/ 025993.

It will be appreciated that the disclosed and described systems and methods in this patent specification are designed to condense the image information made available from a tomosynthesis reconstruction volume (or "stack") containing 3D breast image data down to a set of synthesized 2D images, similar to conventional 2D mammographic images. By reviewing these synthesized 2D images concurrently with or without the 3D tomosynthesis stack, it is possible to provide a much more efficient and accurate review of the breast tissue. In embodiments with concurrent review, the synthesized 2D merged images can act as a guidance-map, so that the user reviewing the images can focus on the synthesized 2D images for detecting any objects or regions of interest that merit further review, and the system can provide immediate, automated navigation to a "best" corresponding tomosynthesis image slice (or a subset of adjacent tomosynthesis slices) to allow the user to conduct this further review to verify and evaluate the finding. Thus, it is preferred, although not required for practicing all embodiments, for the user to employ a user interface that can display a respective synthesized 2D merged image along-side the tomosynthesis volume image slices, for concurrent viewing of both.

The plurality of 2D and/or 3D images from which the synthesized 2D images are generated may include tomosynthesis projection images, tomosynthesis reconstruction slices, mammography images, contrast enhanced mammography images, synthesized 2D images, and combinations thereof. It will be appreciated that the synthesized 2D images advantageously incorporate the most relevant information from each of the underlying acquired and computer generated image data sets of the respective breast. Thus, different regions of pixels in the displayed synthesized 2D images may be sourced from corresponding different images in the underlying image data set, depending on which underlying image is best for viewing an object of interest, e.g., a mass or a calcification, in the respective region. The particular regions may be identified statically, i.e., within a particular grid, or dynamically, i.e., based on identified objects of interest, and may range in granularity from as little as one pixel, to all pixels in the respective image. In one embodiment, priority is given to first importing into a merged image under construction those regions containing one or more specific tissue structures of interest in the images of a tomosynthesis image data set (or "stack"), and thereafter populating the remaining regions of the merged image with the otherwise most relevant regions from the images, as described above.

The user interface may additionally include features to enable the user to manipulate the presented tomosynthesis data, for example, to allow the user to scan through adjacent image slices of the tomosynthesis stack, or to further zoom (magnify) into a selected region, to place markers, or alternatively to apply filters or other image processing techniques to the image data. In this manner, the user may quickly review a large stack of tomosynthesis data by utilizing the synthesized 2D images for navigation purposes, thereby increasing the performance and efficiency of breast cancer screening and diagnosis. According to another embodiment, it has been determined or otherwise appreciated that particular types of images may include or be superior for viewing different types of relevant information. For example, calcifications are typically best visualized in 2D mammograms, while masses are typically best visualized using 3D reconstructed images.

Thus, in one embodiment, different filters are applied to each of the different types of underlying 2D and/or 3D images in the image data set used to generate the merged images, the filters selected to highlight particular characteristics of the images that are best displayed in the respective imaging modes. Appropriate filtering of the images prior to generating the merged images helps ensure that the final merged images include the most relevant information that can be obtained from all the underlying image types. Additionally and/or alternatively, the type of filtering performed for the various images may be defined via user input, which permits a user to select a 'merge mode', for example, geared towards highlighting masses, calcifications, or for making the merged images appear to be a particular image type, such as a 3D reconstructed slice, or a 2D mammogram.

Synthesizing the 2D images may be accomplished in a variety of ways. For example, in one embodiment, general purpose image filtering algorithms are used to identify features within each of the respective source 2D and 3D images, and a user may select whether to use 2D filtered data and/or 3D filtered data to generate the merged images. Alternatively, 2D or 3D filtered data may be automatically selected in accordance with a particular visualization mode that has been user selected; for example, 2D filtered data may be automatically selected by the system for calcification visualization mode, while 3D filtered data may be automatically selected by the system for mass visualization modes. In one embodiment, two different sets of merged images may be constructed, one for each mode; alternatively, a single set of merged images may be constructed that takes into account the respective filtered image data results from all available image types.

In one embodiment, features (representing potential objects of interest) are identified in the available source images and thereafter weighted, e.g., on a pixel by pixel or region by region basis in each respective image. A 2D image is then constructed by incorporating the respective regions having the most significant weight in individual images of the available source images. The size of the region may vary in granularity from one pixel to many (or even all) pixels of the respective image, and may be statically pre-defined, or may have margins that vary in accordance with the varying thresholds of the source images. The synthesized (aka "merged") image may be pre-processed and stored as a DICOM object following tomosynthesis acquisition, and thereafter forwarded with the reconstruction data for subsequent review by a user. Such an arrangement removes the need to forward weighting information for each reconstructed slice. Alternatively, the stored DICOM object may include the weighting information, allowing the merged images to be dynamically constructed in response to a request for synthesized 2D images at the user's work station. In one embodiment, both the weighting information and the synthesized 2D image may be provided in the DICOM object, allowing presentation of a default set of merged images, while still enabling customization according to the personal workflow of the reviewer. To be clear, the weighting information can be stored with the image itself, and need not be a separate file.

The weighing or enhancement of features in the source images may be modified based on the number of Tr slices from which synthetic $I_{MERGE}$ slabs are generated. For instance, a factor, coefficient, value, or weight used to weigh a feature in a source image may result in more weighing of the feature in a Tr slice when the slab is to be generated from 30 slices, when compared to the weighing of the same feature in the same Tr slice when the slab is to be generated from 10 slices. Further, the selection of features to be weighed may be modified based on the number of Tr slices from which synthetic $I_{MERGE}$ slabs are generated. For instance, more features may be weighed or enhanced when more a slab is generated from more slices. The weighing factors can be predetermined and stored in a look-up table in the system. Alternatively, the weighing factors can be empirically or mathematically determined from the number of Tr slices from which synthetic $I_{MERGE}$ slabs are to be generated. In this manner, the features from the source Tr slices can be enhanced in the synthetic $I_{MERGE}$ slabs. The synthetic $I_{MERGE}$ slabs can present enriched information by combining clinically relevant features from multiple Tr slices and highlighting same. Such slabs can be used to drive further image processing and analytics, and provide enhanced data review performance and increase efficiency and throughput.

It is realized that the visualization of the synthesized 2D images may have some drawbacks. For example, there may be neighboring regions in a merged image which exhibit bright calcifications, but which in fact are sourced from image slices that are distant from one another in the z plane. Therefore, what may appear to be a cluster of micro-calcifications in a 2D image may, in fact, be individual calcifications that are distributed (i.e., along the z-axis) throughout the breast and thus do not actually represent a micro-calcification cluster that requires further review. Thus, according to another embodiment, a 'cluster spread indicator' may be provided with the synthesized 2D image, which visually indicates the distribution of calcifications along the z-plane, allowing the user to quickly assess whether a group of calcifications comprise a calcification cluster.

The synthesized 2D images are displayed to the user of the described system (e.g., the medical professional or the radiologist), typically on a workstation having side-by-side monitors as depicted in FIG. 5B. Depending on how the user has configured the workstation, when initiating review of particular person's breast image data, only the synthesized 2D images may be presented, e.g., on the left-hand-side monitor, with the right-hand-side monitor being blank, or perhaps depicting a first or middle image slice from the tomosynthesis stack, preferably depending on a user-selectable configuration. In one embodiment, the system will initially and serially display the synthesized 2D images on the left-hand-side monitor, and a "most relevant" one of the tomosynthesis slice images on the right-hand-side monitor, which was determined by the system based upon the displayed tomosynthesis slice being most similar in appearance to each synthesized 2D image, or having the relatively most interesting objects, out of the tomosynthesis image stack for the entire breast volume.

As noted above, in various embodiments, an object or region may be automatically highlighted in the synthesized 2D image and/or displayed at least portion of the one or more images from the plurality. Additionally and/or alternatively, an object or region in the synthesized 2D image and/or displayed at least portion of the one or more images from the plurality may be highlighted in response to a further received user command or to certain user activity detected through the user interface. By way of non-limiting example, an object or region may is highlighted by a contour line representing a boundary of the highlighted object or region. Preferably, the object or region is highlighted in a manner indicating that the highlighted object or region is or contains a specified type of tissue structure.

While the system processes a subset of Tr slices to generate an $I_{MERGE}$ slab, it can incorporate additional information designed to target/highlight certain objects, lesions or regions. The information used to target/highlight these objects can be imported in various forms, such as a binary map of identified objects or regions, or as a continuous map including the probability distribution for certain patterns.

Figure 6:
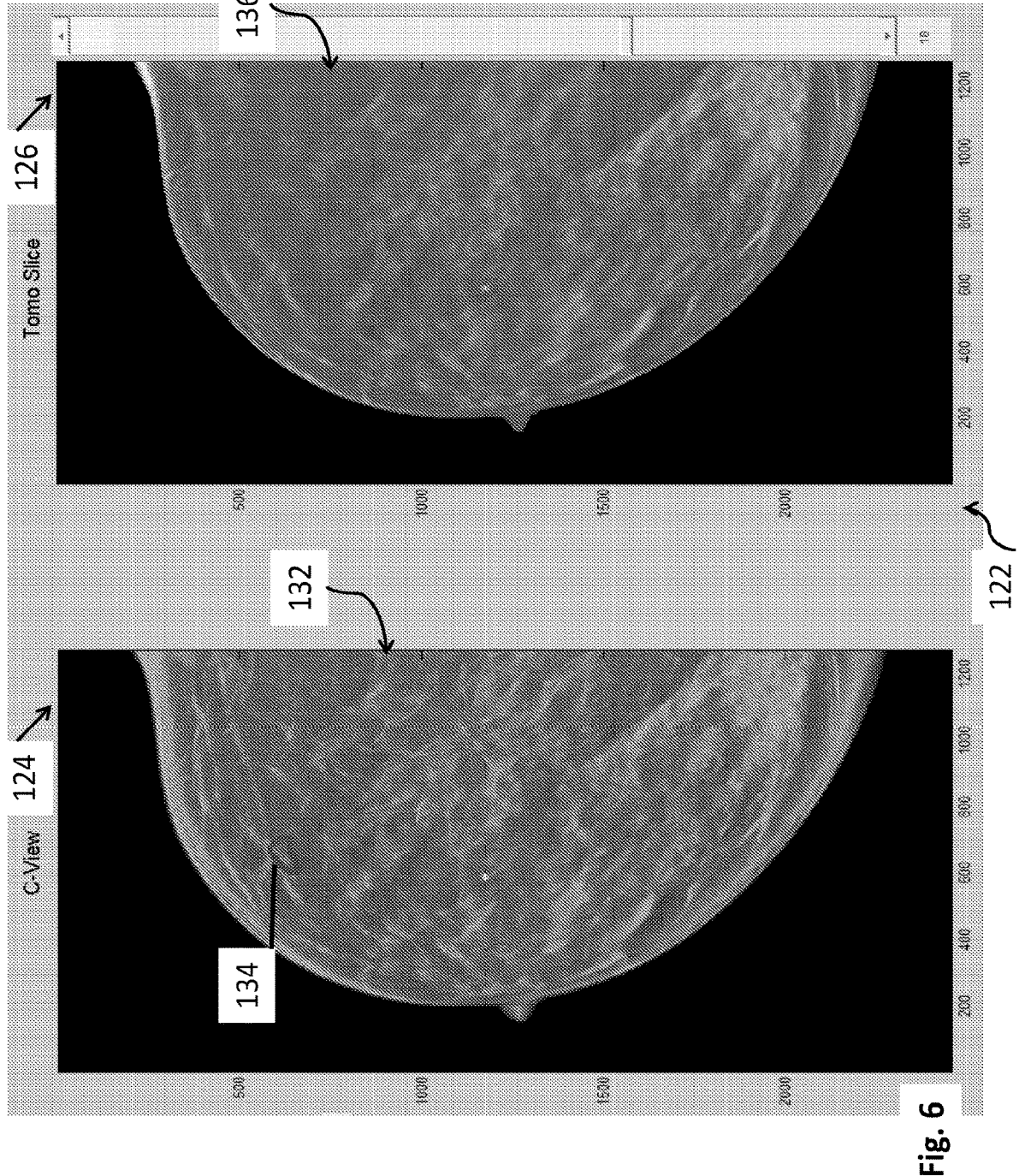
FIG. 6 depicts an exemplary user interface, including a left-hand side monitor displaying a synthesized 2D image of a woman's breast, including a highlighted tissue structure, wherein the highlighting is in the form of a contour line that represents a boundary of the highlighted tissue structure, and a right-hand side monitor displaying the tomosynthesis image from which the highlighted tissue structure was imported into the 2D image, or which otherwise provides a best view of the highlighted tissue structure.

By way of illustration, FIG. 6 depicts an exemplary work station display 122, including a left-hand side monitor 124 ("C-View") displaying one 132 of a plurality of synthesized 2D images of a woman's breast. The synthesized 2D image 132 includes a highlighted tissue structure 134, wherein the highlighting is in the form of a contour line that represents a boundary of the tissue structure. This highlighting may have been done automatically by the system, e.g., at the time the 2D image 132 is initially displayed, or only in response to a specific user command or indication, e.g., by hovering a pointer over the object 134 in the 2D image 132. The work station display 122 also includes a right-hand side monitor 126 displaying the respective tomosynthesis image 136 (which is slice no. 18 of the tomosynthesis volume stack, as indicated in the lower right hand side of the monitor 126), which is the source image or which otherwise provides a most similar view of the highlighted tissue structure 134 as seen in the synthesized image 132. In particular, the user interface associated with the display 122 allows for a user to select or otherwise indicate a location on the synthesized 2D image 132, e.g., by displaying a pointer, a cross, a circle, or other similar geometrical object, and then input a certain command type (e.g., mouse click) that will be recognized by the system as a request from the user to have the corresponding source or otherwise most similar tomosynthesis slice(s) depicting the region or object underlying the pointer displayed in monitor 126.

Figure 7:
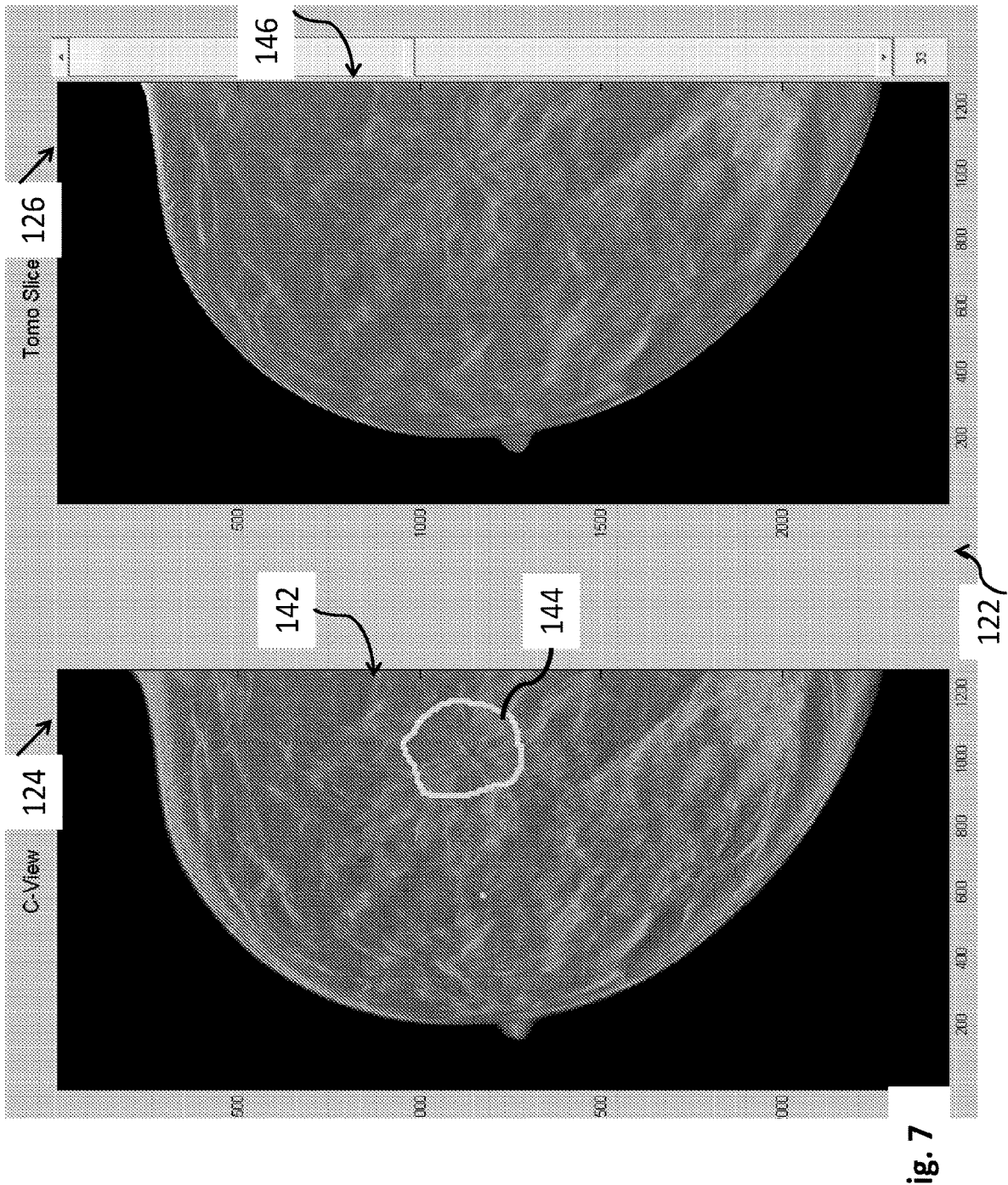
FIG. 7 depicts the user interface of FIG. 6, again displaying a synthesized 2D image of a woman's breast including a highlighted spiculated mass in the left-hand monitor, and a right-hand side monitor displaying the tomosynthesis image from which the depicted spiculated mass was imported into the 2D image, or which otherwise provides a best view of the spiculated mass.

FIG. 7 depicts the work station display 122, wherein a different one 142 of the plurality of synthesized 2D breast images is displayed in the left-hand side C-View monitor 124. The synthesized 2D image 142 includes a highlighted tissue structure 144, wherein the highlighting is in the form of a geometric shape, in this case a circle, to indicate that the object 144 is a spiculated mass. Again, this highlighting may have been done automatically by the system, e.g., at the time the 2D image 142 is initially displayed, or only in response to a specific user command or indication, e.g., by hovering a pointer over the object 144 in the 2D image 142. The right-hand side monitor 126 is displaying the respective tomosynthesis image 146 (which is slice no. 33 of the tomosynthesis volume stack, as indicated in the lower right hand side of the monitor 126), which is the source image or which otherwise provides a most similar view of the highlighted tissue structure 144 as seen in the synthesized image 132.

Figure 8:
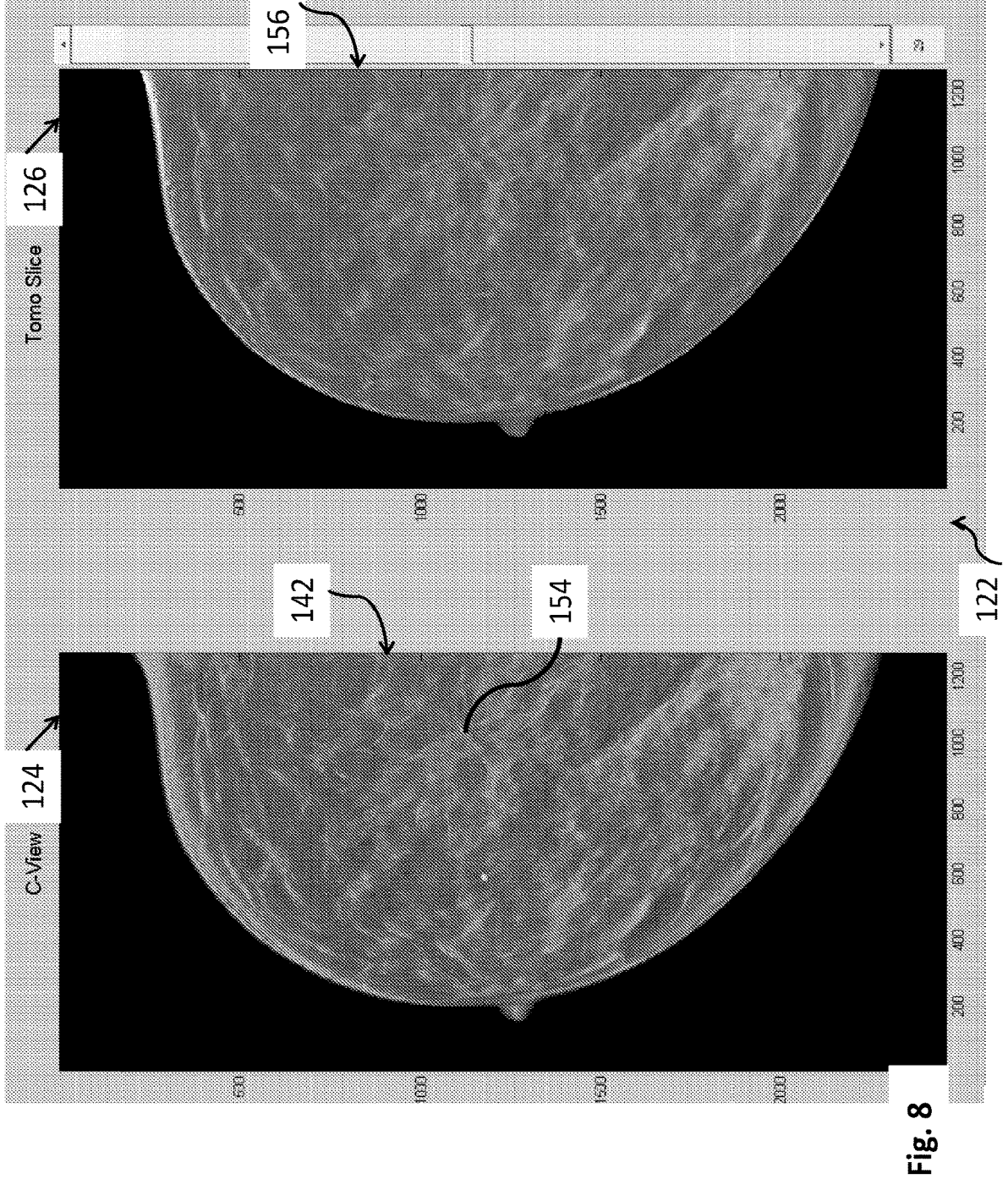
FIG. 8 depicts the user interface of FIG. 7, including the same breast image displayed in the left-hand side monitor, but now highlighting a region containing micro-calcifications, with the right-hand side monitor displaying the tomosynthesis image from which the highlighted region containing the micro-calcifications was imported into the 2D image, or which otherwise provides a best view of the micro-calcifications.

It should be appreciated that there will be instances in which the mapping between an object or region in a merged 2D image to the respective object or region in the displayed (i.e., source or "best") image may not necessarily be 1-to-1, and will possibly be "1-to-many" in certain circumstances, for example, when multiple line structures on different tomosynthesis image slices combine together to form a line-crossing structures in the synthesized 2D image. By way of example, FIG. 8 depicts the user work station display 122, including the same synthesized 2D breast image 142 as displayed in FIG. 7, but now highlighting a region 154 containing micro-calcifications, with the right-hand side monitor displaying the tomosynthesis image slice 156 (which is slice no. 29 of the tomosynthesis volume stack, as indicated in the lower right hand side of the monitor 126), from which the highlighted region 154 was imported into the 2D image 142, or which otherwise provides a best view of the micro-calcifications. In particular, because the spiculated mass structure 144 and region of micro-calcifications 154 are in very close proximity in FIG. 8, a different one may be highlighted depending on a specific user command (e.g., to highlight a certain tissue type), or by slight adjustment of the position of the pointer of the user interface.

The above described examples with respect to FIGS. 6-8 are readily accomplished by index maps or a full 3D map constructed at the same time (or after—depending on the system implementation) the synthesized 2D images are generated, as described in above-referenced PCT Application Nos. PCT/US2012/066526 and PCT/US2013/025993. Alternatively, if no index map or full 3D map is available, for any given such user selected/specified point/location on the 2D image displayed in the left-hand-side monitor 124, the system may execute an algorithm to automatically compute the best corresponding image (i.e., X, Y and Z) within the tomosynthesis stack for display on the right-hand-side monitor 126. A "tomosynthesis slice indicator" may optionally be provided on the left-hand-side monitor 124, which indicates which tomosynthesis slice number (numbers) would be displayed on the right-hand-side monitor 126 based on a current location of a user curser on the 2D image. With this feature, the user need not be distracted by constantly changing image displays on the right-hand-side monitor 126, while still providing the reviewer with an understanding of the z-axis location in the tomosynthesis volume stack of a particular object in a 2D image.

In accordance with one embodiment of the disclosed inventions, the available features of the user interface may be extended to function, not only based on a point/location in a merged image, but also based, in a similar fashion, on a structure/object/region in a merged image. For example, particular objects or regions in a merged image may be automatically highlighted when displayed, based on the system recognition of possible interest in the respective objects, or of objects located in the respective regions. In one embodiment, shown in FIG. 8, this highlighting is in the form of a contour line 108 that represents a boundary of a highlighted tissue structure. A contour line may be similarly used to highlight regions of interest in the displayed image, e.g., containing a number of calcification structures. In some embodiments, the system is configured to allow the user to "draw" a contour line on the merged images as a way of selecting or otherwise indicating an object or region of interest for causing the system to concurrently display one or more underlying source images of the selected or indicated object or region.

In other embodiments, the system employs known image processing techniques to identify different breast tissue structures in the various source images, and highlight them in the merged images, in particular, tissue structures comprising or related to abnormal objects, such as micro-calcification clusters, round-or-lobulated masses, spiculated masses, architectural distortions, etc.; as well as benign tissue structures comprising or related to normal breast tissues, such as linear tissues, cysts, lymph nodes, blood vessels, etc. Further, an object or region consisting of or containing a first type of tissue structure may be highlighted in a first manner in a displayed merged image, and an object or region consisting or containing a second type of tissue structure may be highlighted in a second manner different from the first manner in the displayed merged image.

In various embodiments, the user may input a command through the user interface selecting or otherwise identifying a certain type of tissue structure, and, in response to the received command, the system performs one or both of (i) automatically highlighting in a displayed merged image objects comprising the selected type of tissue structure and/or regions containing one or more objects comprising the selected type of tissue structure, and (ii) automatically concurrently displaying the respective source slice (or otherwise the slice with best depiction of) a tissue structure of the selected type in the breast image data, e.g., a most prominent one of the selected tissue structure type based on a comparison, if more than one is detected in the source image stack. Thus, when the user "click" on (or very close to) a micro-calcification spot/cluster in a merged 2D image, and the system automatically concurrently displays the source (or otherwise best) tomosynthesis image slice including the corresponding micro-calcification in 3D. By way of another example, a user can select (through the user interface) a region in a merged 2D image that has the appearance with radiating line patterns (often an indication of spiculated masses), and the system will concurrently display the source (or otherwise best) 3D tomosynthesis slice, or perhaps to a series of consecutive tomosynthesis slices, for viewing the radiating line patterns.

FIGS. 3 and 5-8 depict embodiments in which an image slab, which is synthesized from a subset of the plurality of tomosynthesis image slices, may be used to navigate that subset of tomosynthesis image slices. In a similar manner, an image slab synthesized from an entire stack of tomosynthesis image slices, can be used to navigate a set of image slabs, which are each generated from respective subsets of tomosynthesis image slices. In such a system, when a user reviewing the image slab generated from the entire stack of tomosynthesis image slices identifies an any object or region of interest that merit further review, the system provides immediate, automated navigation to a "best" corresponding image slab (or a subset of adjacent image slabs) to allow the user to conduct this further review to verify and evaluate the finding.

In various embodiments, the user may input a command through the user interface, activating dynamic display functionality, wherein the system automatically highlights those objects and tissue structures that (dynamically) correspond to the location of a user movable input device in a displayed merged image (e.g., a hovering mouse pointer). In such embodiments, the system may further comprise automatically concurrently displaying a respective source image of a highlighted selected tissue structure that corresponds to a given location of a user movable input device in a displayed merged image, again, on a dynamic basis.

In one embodiment, the system can be activated to provide a "shadow" cursor that is displayed on the right-hand-side monitor 126, in a location corresponding to the same (X, Y) location as the user's actual curser on the left-hand-side monitor 124, so that moving the curser around in the 2D image moves the shadow curser in the tomosynthesis image at same X, Y coordinates. The reverse can also be implemented, i.e., with the active user curser operable in the right-hand monitor 126, and the show curser in the left-hand monitor 124. In one implementation, this dynamic display feature allows the system to follow the user's point of interest, e.g. mouse cursor location in a 2D merged image, and dynamically display/highlight the most "meaningful" region(s) underneath in real time. For example, the user can move the mouse (without clicking any button) over a blood vessel, and the system will instantly highlight the vessel contour.

According to yet another aspect of the disclosed inventions, post review storage of the breast image data is done at the slab level, rather than at the individual reconstructed Tr slice level, in order to reflect the same image data that was actually reviewed by the user, and also to greatly reduce the storage capacity needed for storing the breast image data. By way of example, in one embodiment, the system may display a user interface configured to receive input from a user, including a number of Tr slices 10 per slab 30, an amount of overlap between adjacent slabs 30, and a stack size. The system generates the plurality of slabs 30 based on the user input, and the user then views the displayed slabs (or a subset thereof) in order to study the breast image data. Once the user review of displayed slabs is complete, the image data is transmitted for storage (e.g., in the PACS system of a hospital) as a file containing just the generated slabs, and not the underlying full stack of Tr image slices.

Having described exemplary embodiments, it can be appreciated that the examples described above and depicted in the accompanying figures are only illustrative, and that other embodiments and examples also are encompassed within the scope of the appended claims. For example, while the flow diagrams provided in the accompanying figures are illustrative of exemplary steps; the overall image merge process may be achieved in a variety of manners using other data merge methods known in the art. The system block diagrams are similarly representative only, illustrating functional delineations that are not to be viewed as limiting requirements of the disclosed inventions. It will also be apparent to those skilled in the art that various changes and modifications may be made to the depicted and/or described embodiments (e.g., the dimensions of various parts), and that various embodiments according to the invention may combine elements or components of those disclosed embodiments even if not expressly exemplified herein in such combination. Accordingly, the specification and drawings are to be regarded in an illustrative rather than restrictive sense, and the scope of the disclosed inventions is to be defined only by the following claims and their equivalents.

The invention claimed is:

1. A system for processing and storage of breast tissue image data, comprising:
an image viewing device configured to:
retrieve image data of breast tissue from a storage, wherein the image data is stored as a set of one or more image slabs, the set of image slabs collectively depicting the breast tissue and produced by an image processing computer by:
processing the image data to generate a set of reconstructed image slices, the reconstructed image slices collectively depicting the breast tissue;
merging relevant image data from one or more image slices of the set of reconstructed image slices into an image slab that includes the relevant image data, the image slab comprising a constructed 2D image of a portion of the breast tissue; and
storing the image data as the set of one or more image slabs.

2. The system of claim 1, wherein the image viewing device is a separate device from the image processing computer.

3. The system of claim 1, wherein the image processing computer is further configured to present the one or more image slabs to a user for review prior to storing the one or more image slabs.

4. The system of claim 3, wherein storing the image data as the one or more slabs includes manual input received from the user.

5. The system of claim 4, wherein the manual input defines one or more of a stack size associated with the one or more image slabs, a number of reconstructed image slices per image slab, and an amount of overlap between adjacent slabs of the one or more slabs.

6. The system of claim 4, wherein the manual input defines a target slice around which the image slab should be generated and, in response, the image processing computer is configured to generate a new image slab centered on the target slice.

7. The system of claim 1, wherein the set of reconstructed image slices is not stored.

8. The system of claim 7, wherein the set of reconstructed image slices is discarded.

9. The system of claim 1, wherein each image slab of the set of image slabs is constructed from a predetermined number of image slices of the set of reconstructed image slices with a predetermined amount of overlap between adjacent slabs of the set of image slabs.

10. The system of claim 9, wherein one or more of the predetermined number of image slices and the predetermined amount of overlap are determined by user input.

11. The system of claim 1, wherein the image processing computer is further configured to determine the relevant image data by:
determining one or more objects or regions of interest to be enhanced in a subset of the set of reconstructed image slices; and weighing each image of the subset of the set of reconstructed image slices on one of a pixel-by-pixel basis and a region-by-region basis to enhance the one or more objects or regions of interest.

12. The system of claim 11, wherein the image slab is constructed by incorporating regions of image slices of the set of reconstructed image slices based on a weight of individual objects of the regions.

13. The system of claim 12, wherein the weight of individual objects of the regions is adjusted based on a number of image slices incorporated into the image slab.

14. The system of claim 11, wherein determining the one or more objects or regions of interest to be enhanced comprises applying a CAD algorithm to image slices of the set of reconstructed image slices.

15. The system of claim 1, further comprising generating an index map associated with the image slab, the index map identifying a source image for the relevant image data.

16. A method for processing and storage of breast tissue image data, comprising:
receiving image data of breast tissue;
processing the image data to generate a set of reconstructed image slices, the reconstructed image slices collectively depicting the breast tissue;
merging relevant image data from one or more image slices of the set of reconstructed image slices into an image slab that includes the relevant image data, the image slab comprising a constructed 2D image of a portion of the breast tissue; and
storing the image data as a set of image slabs for subsequent viewing, the set of image slabs collectively depicting the breast tissue.

17. The method of claim 16, wherein the one or more image slabs comprise a set of image slabs, the set of image slabs collectively depicting the breast tissue.

18. The method of claim 17, wherein each image slab of the set of image slabs is constructed from a predetermined number of image slices of the set of reconstructed image slices with a predetermined amount of overlap between adjacent slabs of the set of image slabs.

19. The method of claim 16, further comprising determining the relevant image data by:
determining one or more objects or regions of interest to be enhanced in a subset of the set of reconstructed image slices; and
weighing each image of the subset of the set of reconstructed image slices on one of a pixel-by-pixel basis and a region-by-region basis to enhance the one or more objects or regions of interest.

20. A system for processing breast tissue image data for storage, comprising:
an image processing computer configured to:
receive image data of breast tissue;
process the image data to generate a set of reconstructed image slices, the reconstructed image slices collectively depicting the breast tissue;
merge relevant image data from one or more image slices of the set of reconstructed image slices into an image slab that includes the relevant image data, the image slab comprising a constructed 2D image of a portion of the breast tissue; and
store the image data as a set of image slabs for subsequent viewing, the set of image slabs collectively depicting the breast tissue.

* * * * *